United States Patent
Nicoll et al.

(10) Patent No.: US 9,193,948 B2
(45) Date of Patent: *Nov. 24, 2015

(54) BIOMATERIALS FOR TISSUE REPLACEMENT

(75) Inventors: Steven B. Nicoll, New York, NY (US);
Simone S. Stalling, Pittsburgh, PA (US);
Anna T. Reza, North Bethesda, MD (US)

(73) Assignee: The Trustees of The University of Pennsylvania, Philadelphia, PA (US)

( * ) Notice: Subject to any disclaimer, the term of this patent is extended or adjusted under 35 U.S.C. 154(b) by 82 days.

This patent is subject to a terminal disclaimer.

(21) Appl. No.: 13/129,058

(22) PCT Filed: Nov. 12, 2009

(86) PCT No.: PCT/US2009/064254
§ 371 (c)(1),
(2), (4) Date: Aug. 26, 2011

(87) PCT Pub. No.: WO2010/056899
PCT Pub. Date: May 20, 2010

(65) Prior Publication Data
US 2011/0301525 A1 Dec. 8, 2011

Related U.S. Application Data

(60) Provisional application No. 61/114,034, filed on Nov. 12, 2008.

(51) Int. Cl.
| | | |
|---|---|---|
| *A61K 35/32* | (2015.01) | |
| *A61K 38/02* | (2006.01) | |
| *A61K 31/765* | (2006.01) | |
| *C12N 5/00* | (2006.01) | |
| *A61L 27/20* | (2006.01) | |
| *A61L 27/38* | (2006.01) | |
| *A61L 27/52* | (2006.01) | |
| *A61L 27/54* | (2006.01) | |

(52) U.S. Cl.
CPC ............... *C12N 5/0068* (2013.01); *A61L 27/20* (2013.01); *A61L 27/3804* (2013.01); *A61L 27/52* (2013.01); *A61L 27/54* (2013.01); *A61L 2300/25* (2013.01); *A61L 2300/252* (2013.01); *A61L 2300/414* (2013.01); *A61L 2300/426* (2013.01); *A61L 2300/43* (2013.01); *A61L 2430/06* (2013.01); *A61L 2430/34* (2013.01); *A61L 2430/38* (2013.01); *C12N 2533/78* (2013.01)

(58) Field of Classification Search
None
See application file for complete search history.

(56) References Cited

U.S. PATENT DOCUMENTS

| | | | |
|---|---|---|---|
| 5,632,774 A | 5/1997 | Babian | |
| 5,837,747 A | 11/1998 | Soon-shiong et al. | |
| 6,262,141 B1 | 7/2001 | Cywar et al. | |
| 6,719,797 B1 | 4/2004 | Ferree | |
| 2002/0131952 A1 | 9/2002 | Hennink et al. | |
| 2003/0138490 A1* | 7/2003 | Hu et al. ............... | 424/486 |
| 2005/0196377 A1* | 9/2005 | Ratcliffe et al. ........... | 424/78.31 |
| 2005/0203206 A1 | 9/2005 | Trieu et al. | |
| 2007/0003525 A1 | 1/2007 | Moehlenbruck et al. | |
| 2007/0020225 A1 | 1/2007 | Abramson et al. | |
| 2007/0098675 A1* | 5/2007 | Elisseeff et al. ............. | 424/78.3 |
| 2007/0110788 A1 | 5/2007 | Hissong et al. | |
| 2007/0134291 A1 | 6/2007 | Ting et al. | |
| 2007/0212385 A1 | 9/2007 | David et al. | |
| 2007/0269518 A1* | 11/2007 | Walline et al. ................ | 424/484 |
| 2008/0193536 A1 | 8/2008 | Khademhosseini et al. | |

OTHER PUBLICATIONS

Marsano et al., "Cellulose methacrylate: synthesis and liquid crystilline behaviour of solutions and gels", Polymer vol. 39, issue 18, 1998, pp. 4289-4294.
Nguyen et al., "Photopolymerizable hydrogel for tissue engineering applications" Biomaterials vol. 23, issue 22, 2002, pp. 4307-4314.
Ruel-Gariepy et al., "In situ-forming hydrogels—review of temperature sensitive systems", Eur. J. Pharm. Biopharm. 2004, 58(2):409-426.
Van Tomme et al., "In situ gelling hydrogels for pharmaceutical and biomedical applications", Int. J. Pharm. 2008, 355(1-2) : 1-18.

* cited by examiner

*Primary Examiner* — H. Sarah Park
(74) *Attorney, Agent, or Firm* — Mark S. Cohen; Pearl Cohen Zedek Latzer Baratz LLP

(57) ABSTRACT

This invention relates to biomaterial compositions, methods and kits for producing hydrogels with tunable physico-chemical properties. Specifically, the invention relates to producing cellulosic hydrogels having optimized physico-chemical properties enabling support of cell growth or as replacement or filler for tissue repair, reconstruction or augmentation.

29 Claims, 24 Drawing Sheets

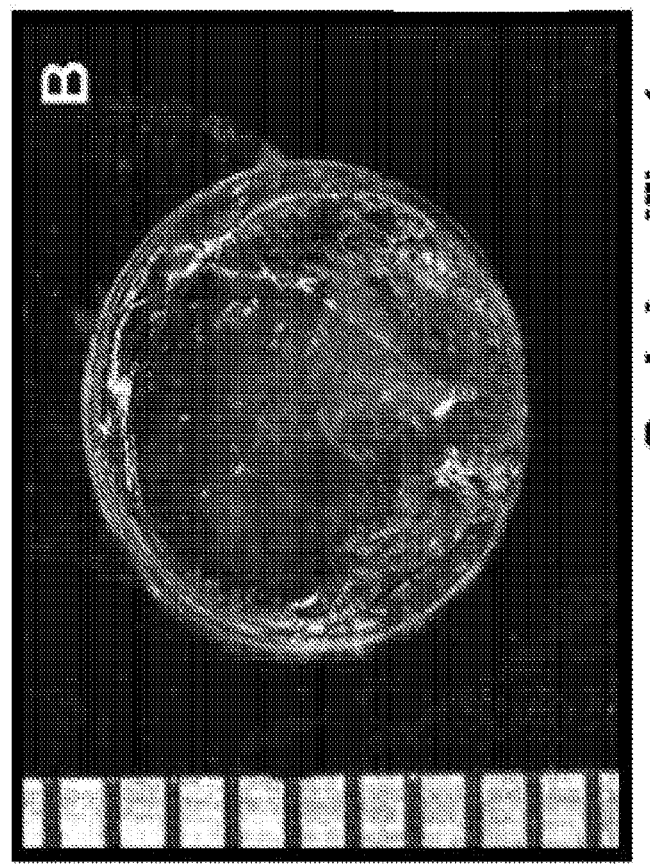
Figure 9

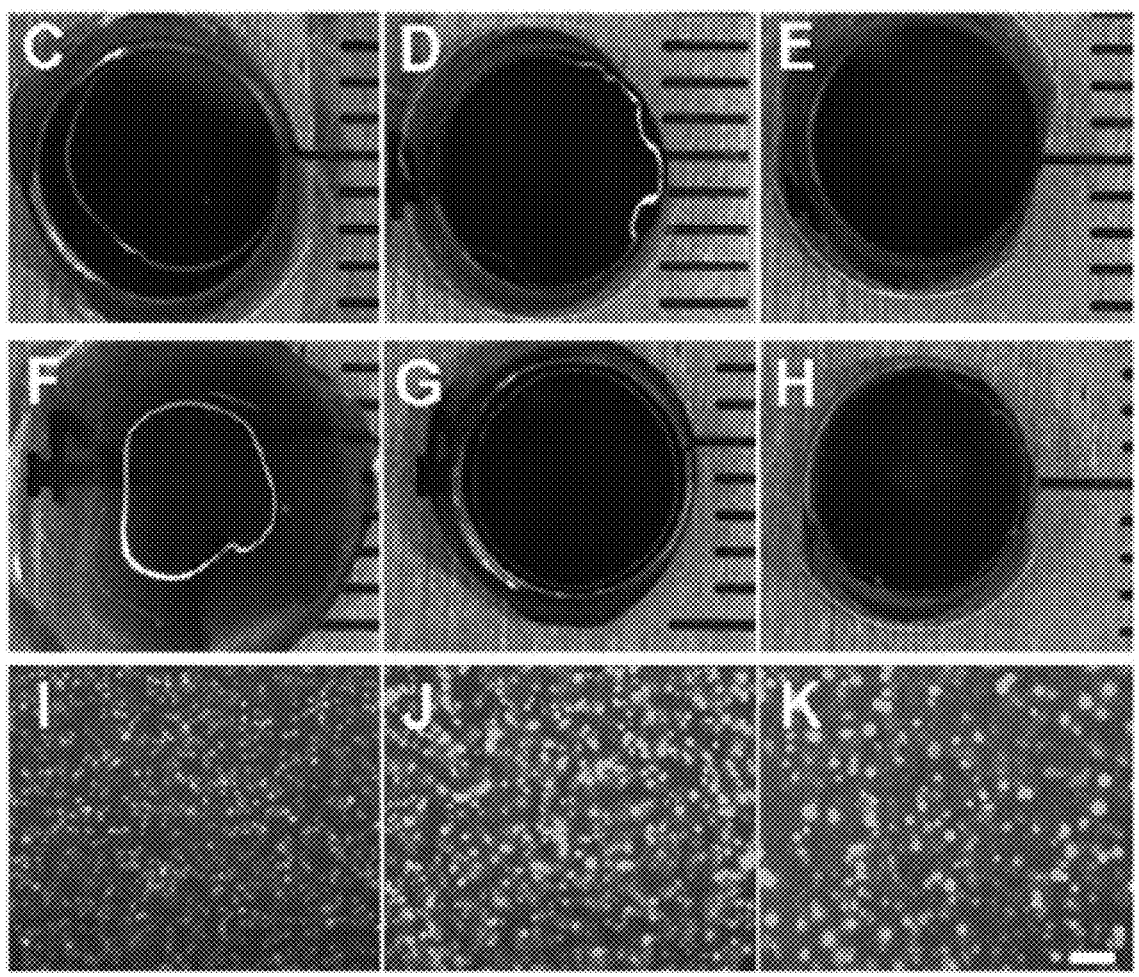
FIG. 15C-K

+ Significant vs. corresponding treated group within time point (i.e., DMEM vs. DMEM+)
Significant vs. opposing media type within time point (i.e., DMEM+ vs. CDM+)

Day 28 Mechanics and Stereoscope Images. Scale in mm

+ Significant vs. corresponding treated group within time point (i.e., DMEM vs. DMEM+)
Significant vs. opposing media type within time point (i.e., DMEM+ vs. CDM+)

Day 28 Col I biochemistry (A) and IHC (B-E). Bar = 50 um

+ Significant vs. corresponding treated group within time point (i.e., DMEM vs. DMEM+)
Significant vs. opposing media type within time point (i.e., DMEM+ vs. CDM+)

Day 28 Col II biochemistry (A) and IHC (B-E). Bar = 50 um

Day 28 Aggrecan IHC – 20X magnification
Center of sample pictures

|  | Diameter (mm) | Thickness (mm) |
|---|---|---|
| DMEM | 5.53 ± 0.09 + | 2.44 ± 0.06 + |
| DMEM+ | 6.39 ± 0.07 # | 2.89 ± 0.07 # |
| CDM | 5.65 ± 0.09 + | 2.48 ± 0.04 + |
| CDM+ | 6.62 ± 0.05 # | 3.48 ± 0.10 # |

+ Significant vs. corresponding treated group within time point
Significant vs. opposing media type within time point Day 28 Diameter and Thickness

Figure 22

|  |  | Wet Weight (mg) | Dry Weight (mg) | $Q_w$ | DNA/Wet Weight (ng/mg) |
|---|---|---|---|---|---|
| DMEM | D3 | 64.54 ± 3.23 | 1.68 ± 0.35 | 39.4 ± 6.1 | 67.6 ± 3.7 * + |
|  | D14 | 67.99 ± 2.36 + | 1.76 ± 0.09 + | 38.8 ± 2.8 + | 31.7 ± 4.9 + # |
|  | D28 | 67.84 ± 0.91 + | 1.94 ± 0.24 + | 35.5 ± 4.6 + | 28.9 ± 3.2 + # |
| DMEM+ | D3 | 63.65 ± 4.79 * | 1.65 ± 0.20 * | 38.8 ± 2.4 * | 130.6 ± 7.9 * |
|  | D14 | 80.14 ± 1.21 * # | 3.03 ± 0.16 * # | 26.5 ± 1.7 | 277.1 ± 12.2 # |
|  | D28 | 92.60 ± 2.76 * # | 4.08 ± 0.09 * # | 22.7 ± 0.9 | 272.0 ± 14.2 # |
| CDM | D3 | 64.30 ± 3.19 | 1.73 ± 0.08 | 37.3 ± 3.3 | 83.4 ± 3.5 † |
|  | D14 | 66.52 ± 6.88 + | 1.75 ± 0.23 + | 38.1 ± 2.3 + | 59.2 ± 8.8 + # |
|  | D28 | 71.41 ± 1.17 + | 1.80 ± 0.04 + | 39.8 ± 1.5 + | 71.0 ± 2.3 + # |
| CDM+ | D3 | 67.84 ± 4.22 * | 1.96 ± 0.06 * | 34.7 ± 1.7 * | 108.8 ± 18.6 |
|  | D14 | 108.74 ± 0.96 * # | 4.19 ± 0.20 * # | 26.0 ± 1.2 | 97.0 ± 4.6 # |
|  | D28 | 127.18 ± 4.11 * # | 5.73 ± 0.13 * # | 22.2 ± 0.5 | 155.3 ± 4.9 * # |

\* Significant vs. all other time points within group
\+ Significant vs. corresponding treated group within time point (i.e., DMEM vs. DMEM+)
\# Significant vs. opposing media type within time point (i.e., DMEM+ vs. CDM+)
† Significant vs. D14 within group

Figure 23

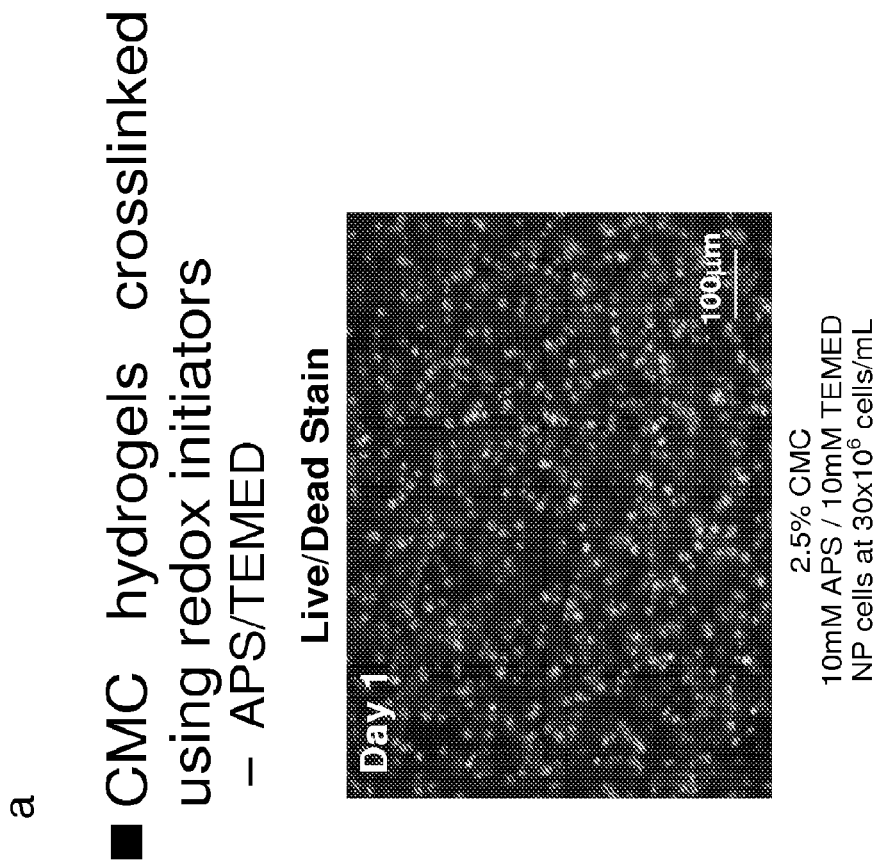
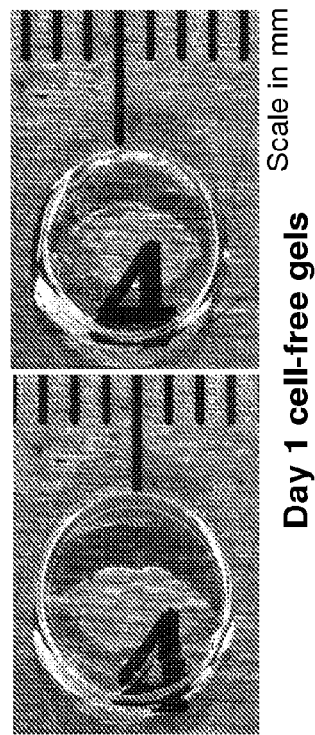
Figure 25

BIOMATERIALS FOR TISSUE REPLACEMENT

CROSS REFERENCE TO RELATED APPLICATIONS

This application is a National Phase Application of PCT International Application PCT/US09/64254, filed Nov. 12, 2009 that claims priority to U.S. Provisional Patent Application 61/114,034, filed Nov. 12, 2008, both of which are incorporated herein by reference in their entirety.

GOVERNMENT INTEREST

The invention was supported, in part, by Grant Number 0747968 from the National Science Foundation. The United States government may have certain rights in the invention.

FIELD OF THE INVENTION

The invention relates to biomaterial compositions, methods and kits for producing hydrogels with tunable physicochemical properties. Specifically, the invention relates to producing cellulosic hydrogels having optimized physicochemical properties enabling support of cell growth or as replacement or filler for tissue repair, reconstruction or augmentation.

BACKGROUND OF THE INVENTION

There is much interest within the medical community for materials and methods for use in reconstructive surgery of tissue. An emerging approach is tissue engineering, in which new tissue is grown from tissue-comprising biomaterials and engineered into desired shapes and structures. The types of tissues that can be grown and engineered include, for example, bone, and cartilage. One of the primary uses for replacement cartilage is to correct defects in the articular surface of various joints. For example, a damaged cartilage meniscus in a patient's knee can be replaced with an artificially engineered meniscus.

Likewise, new biomaterials for soft tissue augmentation are in demand given the limitations of current materials and the surge in elective and non-elective surgical procedures to correct contour defects and for tissue replacement. Autogenous fillers such as fat tissue are beneficial but not ideal in that they are associated with donor site morbidity, resorption, migration and supply limitations. Numerous natural and synthetic biomaterials have emerged with different compositions and preparations to meet the growing demands of physicians and patients. The duration of the effect (temporary, semi-permanent and permanent) is often used to categorize these commercialized products. In the United States, permanent fillers are composed of a variety of biomaterials such as poly(methylmethacrylate), polymeric silicone, poly(tetrafluoroethylene) and polyethylene. These implantable materials can lead to adverse clinical outcomes including recurrent hematomas, edema, hypertrophic scarring, nodule formation and resorption. As such, there is a tremendous need for safe and effective biomaterials for dermal implant and filler applications that minimize deleterious tissue responses.

SUMMARY OF THE INVENTION

In one embodiment, the invention provides a biomaterial composition comprising a cellulose derivative polymer wherein an unprotected group on the cellulose derivative polymer backbone is substituted with covalently bound photocrosslinkable groups, or redox-crosslinkable groups; and an initiator.

In another embodiment, the invention provides a method of modifying a physico-chemical property of a cellulose derivative polymer biomaterial comprising the step of covalently substituting an unprotected group on the cellulose derivative polymer backbone with photocrosslinkable groups, or redox-crosslinkable groups; in the presence of a photoinitiator, cross-linking the biomaterial; and forming a hydrogel from the substituted cellulose derivative polymer.

In another embodiment, the biomaterials provided in the invention are capable of supporting cell growth.

In another embodiment, the invention provides a method of reconstructing, repairing or augmenting a soft tissue in a subject in need thereof, comprising the step of implanting in an affected area of the soft tissue a biomaterial comprising a methacrylate-substituted cellulose derivative polymer, wherein the methacrylate-substituted cellulose derivative polymer is photocrosslinkable or redox-crosslinkable; in the presence of a photoinitiator, crosslinking the polymer; and forming a hydrogel.

In another embodiment, the invention provides a method of smoothing skin wrinkles in a subject, comprising the steps of: injecting into a skin wrinkle a biomaterial composition comprising a methacrylate-substituted cellulose derivative polymer, wherein the methacrylate-substituted cellulose derivative polymer is photocrosslinkable or redox-crosslinkable; filling the wrinkle with the biomaterial; and exposing the skin to an electromagnetic radiation source, thereby forming a crosslinked hydrogel in-situ.

In another embodiment, the invention provides a method of making an implant for the reconstruction, repair or augmentation of a soft tissue in a subject, comprising the step of: identifying a volume of interest to be repaired, reconstructed or augmented in the subject; filling the volume with a biomaterial, the biomaterial comprising a methacrylate-substituted cellulose derivative polymer, wherein the methacrylate-substituted cellulose derivative polymer is photocrosslinkable or redox-crosslinkable; in the presence of a photoinitiator, crosslinking the polymer; and forming a hydrogel.

In another embodiment, the invention provides a kit for smoothing skin wrinkles in a subject, comprising a biomaterial composition, the composition comprising an injectable polymer suspension wherein the polymer suspension comprises a methacrylate-substituted cellulose derivative polymer photocrosslinkable or redox-crosslinkable; a needle that is adapted for insertion under the surface of the skin, a plurality of syringes that hold the composition; an electromagnetic radiation source; and instructions Other features and advantages of the present invention will become apparent from the following detailed description examples and figures. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The invention will be better understood from a reading of the following detailed description taken in conjunction with the drawings in which like reference designators are used to designate like elements, and in which:

FIG. 9 shows representative gross images of a 6 wt % MC-MA hydrogels (indicated with an arrow) 80 days after implantation subcutaneously in CD1 mice both (A) in vivo and (B) ex vivo;

FIG. 22 shows diameter and thickness measurements of mechanical testing samples (n=5) at day 28 as a function of medium formulation. + Significant vs. corresponding treated Group; # Significant vs. opposing media type.

FIG. 23 shows physical properties (wet weight, dry weight, $Q_w$) and normalized DNA content of CMC constructs (n=4) at days 3, 14, and 28 as a function of medium formulation. * Significant vs. all other time points within group; + Significant vs. corresponding treated group within time point (i.e., DMEM vs. DMEM+); # Significant vs. opposing media type within time point (i.e., DMEM+ vs. CDM+); † Significant vs. D14 within group.

FIG. 25 shows in situ gelation. (A) CMC hydrogels crosslinked using redox initiators (10 mM APS/10 mM TEMED). (B) Elastic modulus at 2% and 2.5% macromer concentration.

DETAILED DESCRIPTION OF THE INVENTION

Figure 1A:
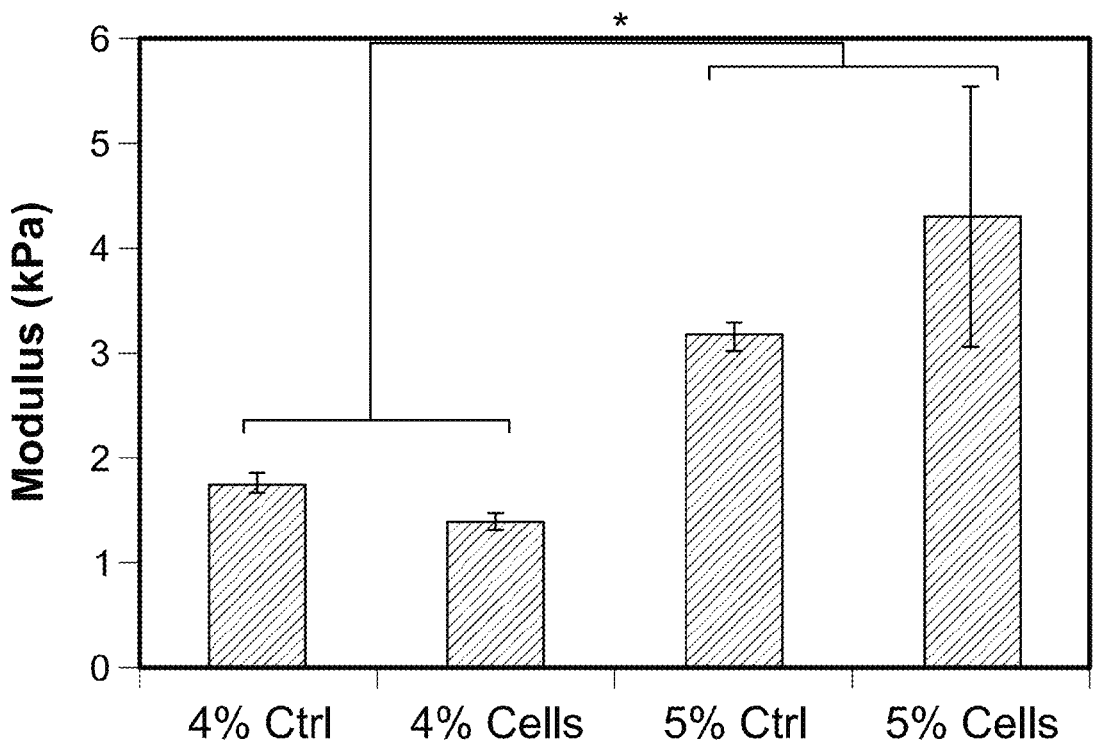
FIG. 1 shows the elastic modulus at day 7 of photocrosslinked low (A) and medium (B) viscosity carboxymethylcellulose (90 and 250 kDa, respectively, at 10% methacrylation) hydrogels encapsulated with bovine nucleus pulposus cells at 30 million cells/mL at various weight percents (w/v). 3% low viscosity CMC hydrogels were structurally stable but too weak for mechanical characterization. 1% medium viscosity CMC hydrogels were amorphous and too weak for mechanical characterization * Significant effect of weight percent.

The invention relates in one embodiment to biomaterial compositions, methods and kits for producing hydrogels with tunable physico-chemical properties. Specifically, the invention relates to biomaterial compositions and methods of producing cellulosic hydrogels having optimized physico-chemical properties enabling support of cell growth or as replacement or filler for tissue repair, reconstruction or augmentation.

A biomaterial useful for soft tissue reconstruction should be safe, biocompatible, easily and reproducibly implemented, non-carcinogenic, effective as a volume-filling material and capable of maintaining its shape. Methods of soft tissue augmentation employ in one embodiment, the use of autogenous adipose tissue as a filler material. In clinical cases of substantial volume loss, such as facial lipoatrophy (LA), donor tissue, which is a temporary filler, is often limited in supply and requires multiple applications. In another embodiment, the photopolymerized methylcellulose hydrogels described in the compositions, kits and methods described herein, are more advantageous for such applications. In one embodiment MA-MC hydrogels maintain their shape with minimal swelling and are non-cytotoxic at all formulations tested with little degradation at higher weight percentages. In vivo, MA-MC hydrogels elicited in one embodiment, a mild inflammatory response, which is particularly beneficial for use in immunocompromised patients that often present with LA following highly active antiretroviral therapy. In one embodiment, the ability to vary solution viscosities and hydrogel stiffness indicates the flexibility of using MA-MC hydrogels in diverse mechanically demanding environments.

In one embodiment, the term "hydrogel" refers to a substance formed when an organic polymer (natural or synthetic) is set or solidified to create a three-dimensional open-lattice structure that entraps molecules of water or other solution to form a gel. The solidification can occur, e.g., by aggregation, coagulation, hydrophobic interactions, or cross-linking.

In another embodiment, the degree of swelling (wet weight/dry weight) and elastic moduli of 2, 4 and 6% (w/v) hydrogels were measured, demonstrating the formation of stable gels with tunable properties. Photocrosslinked methylcellulose hydrogels implanted in one embodiment subcutaneously in NIH-III-Nu mice maintained their integrity and original dimensions after 28 days in vivo. Human dermal fibroblasts encapsulated in 2% (w/v) photocrosslinked methylcellulose hydrogels were viable with minimal cell death. These initial biocompatibility and characterization studies demonstrate the hydrogels which physico-chemical properties are modified using the methods provided herein, of crosslinked methylcellulose hydrogels are ideal for soft tissue engineering applications.

Cellulose is a naturally occurring polysaccharide obtained from wood pulp and cotton that is FDA-approved, inexpensive and biocompatible. However, the water insolubility of cellulose limits its utility in biomedical applications. Modification of cellulose with hydrophobic side groups disrupts the rigid crystalline structure stabilized by strong intermolecular hydrogen bonding and improves the polysaccharide's water affinity. The simplest derivative of cellulose, methylcellulose (MC), which has methyl groups substituted for hydrogens, forms a clear, viscous polymer in an aqueous environment.

Similar to cellulose, MC is also a non-toxic, biocompatible FDA-approved material. Methylcellulose is useful for a variety of applications because of its low cost and its unique ability to gel at elevated temperatures. Nevertheless, methylcellulose (MC) hydrogels formed by thermal gelation have limited long-term mechanical integrity in that the gelation process is easily reversed by subsequent reduction in temperature. The thermoreversibility of MC has been exploited for the manufacturing of medicinal capsules and tablet coatings, but is insufficient for other biomedical applications requiring stable gel formation with greater mechanical strength.

Photopolymerization refers in one embodiment, to an effective method to covalently crosslink polymer chains, producing stable three-dimensional hydrogel networks of varying geometries and physico-chemical properties. In one embodiment, polymers are modified with functional groups (i.e., methacrylates in one embodiment) that undergo free radical polymerization in the presence of a photo-initiator and upon exposure to light. In another embodiment, the polymerization reaction used in the methods described herein, induces a sol-gel phase transformation under physiologic conditions and is ideal in one embodiment, for in vivo crosslinking of injectable polymers. Specific photoinitiators, such as IRGA-CURE® 2959 (Ciba Specialty Chemicals, Basel, Switzerland) are effective with no apparent cytotoxic effects. In one embodiment, UV light penetrates the skin to a depth of about 2 mm in one embodiment, it allows for transdermal photopolymerization of injected polymers.

Accordingly and in one embodiment, provided herein is a biomaterial composition comprising a cellulose derivative polymer wherein an unprotected group on the cellulose derivative polymer backbone is substituted with a covalently bound photocrosslinkable groups, or redox-crosslinkable groups; and an initiator.

Cellulose refers in one embodiment to a Cellulose that is a linear polymer of β-(1→4)-D-glucopyranose units in $^4C_1$ conformation, with each cellulose molecule having three hydroxyl groups per monomer, with the exception of the terminal ends. Chemical modification of cellulose is performed in one embodiment, to improve processability and to produce cellulose derivatives which in another embodiment are referred to as "cellulosics" that, in another embodiment, are tailored for specific applications.

In one embodiment, cellulose derivitization involves esterification or in another embodiment, etherification of the hydroxyl groups on the cellulose chain. In another embodiment, cellulose ethers are manufactured through alkali reactions and are typically water soluble and are used in one embodiment, to modify the rheological properties in predetermined applications. In one embodiment, the cellulose ethers used in the methods compositions and implants described herein, are methyl cellulose (MC), hydroxyethyl cellulose (HC), carboxymethyl cellulose (CMC), or any combination thereof.

In another embodiment, biomaterial compositions comprising the cellulose derivatives are cellulose ethers whose water solubility is achieved by etherification with hydroxyalkyl groups and/or with alkyl groups. In another embodiment, the cellulose derivatives are derivatives of hydroxyethyl cellulose (HEC) or of methyl cellulose (MC). In one embodiment MC is used as mixed ether with hydroxyalkyl groups (methyl hydroxyalkyl celluloses). Mixed ethers of methyl cellulose which may be mentioned here are, in particular, methyl hydroxyethyl cellulose (MHEC), methyl hydroxypropyl cellulose (MHPC) and methyl hydroxyethyl hydroxypropyl cellulose (MHEHPC) or a combination thereof in other discrete embodiments.

In one embodiment, biomaterial compositions comprising the methycellulose (MC) modified using the methods described herein has the following general formula:

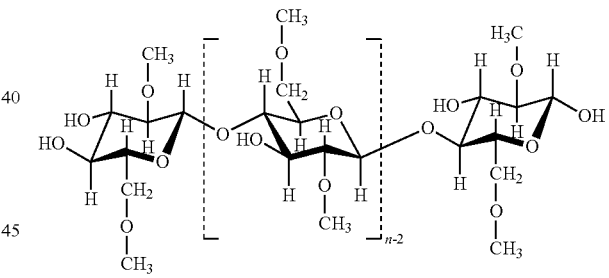

In one embodiment, the crosslinking substituents are esterified to position 6 on the cellulose backbone.

In another embodiment, the Hydroxypropyl Methylcellulose (HPMC) modified using the methods described herein has the following general formula:

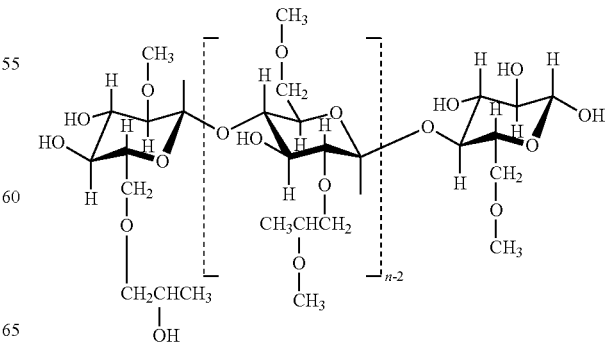

In another embodiment, the crosslinking agents used in the methods described herein to modify the HPMC hydrogels described herein, are esterified to any free hydroxyl group on the cellulosic backbone.

In another embodiment, the carboxymethylcellulose (CMC) modified using the methods described herein has the following general formula:

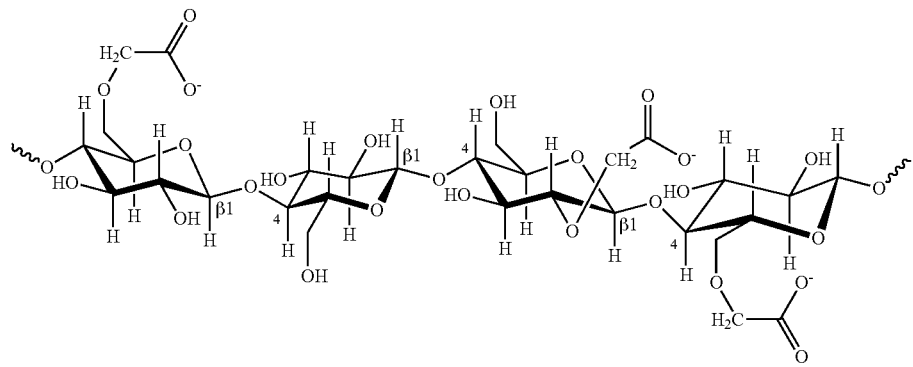

In another embodiment, the crosslinking agents used in the methods described herein modify the CMC hydrogels described herein, are esterified to any free hydroxyl group on the cellulosic backbone.

In another embodiment, the ethyl(hydroxyethyl) cellulose (EHEC) modified using the methods described herein has the following general formula:

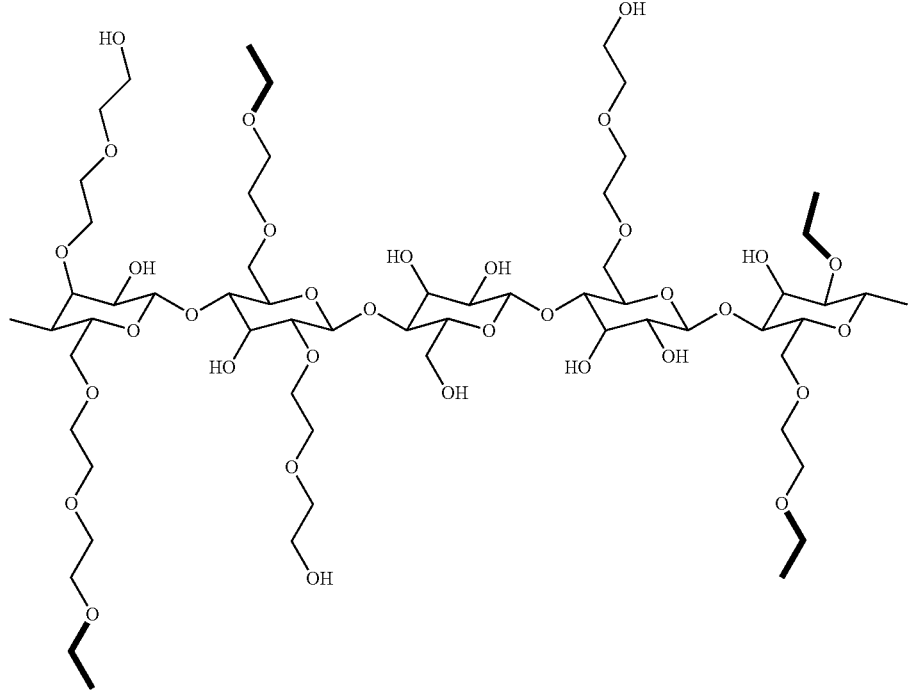

In another embodiment, the crosslinking agents used in the methods described herein to modify the EHEC hydrogels described herein, are esterified to any free hydroxyl group on the cellulosic backbone, or in another embodiment, to the hydroxyl group at the end of the hydroxyethyl substituent.

In other embodiments, the crosslinking substituents used in the preparation of the biomaterial compositions compris-ing the modified hydrogels described herein, are esterified to any unprotected group capable of covalent linking to the functional group of the crosslinking agent.

In one embodiment, the covalently substituted group used as a crosslinking agent to modify the physico-chemical characteristics of biomaterial compositions comprising the the hydrogels described herein, is photocrosslinkable and the step of cross-linking is performed in the presence of a photoinitiator, by exposing the hydrogel to electromagnetic radiation. In another embodiment, the photocrosslinkable group is a methacrylate group.

In one embodiment, the term "crosslinking" refers to the formation of a polymeric network of infinite molecular weight and occurs in polymerizations with reactants having functionalities greater than two. A crosslink is formed in another embodiment, between the radicals generated from the pendent photoinitiator groups and polymerizable functional groups of the crosslinking agent by a chain growth process.

In another embodiment, the photoinitiator is IRGA-CURE® 184, DAROCUR® 1173, and/or IRGACURE®

1750, which in another embodiment, is added at a concentration of about 1 weight %. In another embodiment, the photoinitiator is benzoin methyl ether, or 1-hydroxycyclohexyl phenyl ketone, 2-hydroxy-2-methyl-1-phenylpropane-1-one, 4,4'-azobis(4-cyanovaleric acid), and bis(2,6-dimethoxybenzoyl)-2,4,4-trimethylpentyl phosphine oxide, or their combination in other discrete embodiments. In one embodiment, the photoinitiator is 2-methyl-1-[4-(hydroxyethoxy) phenyl]-2-methyl-1-propanone.

In one embodiment, provided herein is an implant comprising the cellulose derivative hydrogels in which physico-chemical properties were attenuated using the methods described herein. In one embodiment, the implants described herein are used as a dermal filler, or for soft tissue augmentation or their combination in other discrete embodiments of the use of the implants comprising the cellulose derivative hydrogels which physico-chemical properties were attenuated using the methods described herein and the compositions described herein.

In one embodiment, the step of cross-linking the cellulose derivative hydrogels which physico-chemical properties were attenuated using the methods described herein is preceded by a step of casting the hydrogel into a custom mold.

In another embodiment, provided herein is a method of making an implant for the reconstruction, repair or augmentation of a soft tissue in a subject, comprising the step of: identifying a volume of interest to be repaired, reconstructed or augmented in the subject; filling the volume with a biomaterial, the biomaterial comprising a methacrylate-substituted cellulose derivative polymer, wherein the methacrylate-substituted cellulose derivative polymer is photocrosslinkable or redox-crosslinkable; in the presence of a photoinitiator, crosslinking the polymer; and forming a hydrogel.

In one embodiment, provided herein is a novel hydrogel fabricated from methylcellulose (15 kDa) modified with photocrosslinkable methacrylate groups through esterification using methacrylic anhydride. In another embodiment, purified macromer (5% modification) is resuspended in 0.05 wt % of the photoinitiator, 2-methyl-1-[4-(hydroxyethoxy)phenyl]-2-methyl-1-propanone (IRGACURE® 2959), cast into custom molds, and exposed to long wavelength UV light for 10 minutes to form gels.

In one embodiment, the physico-chemical property modified using the methods described herein is a property directed towards changing a viscoelastic parameter of the hydrogels. These parameters are in another embodiment G', or G", tan-d, Young's modulus, glass transition temperature, inherent viscosity, effective molecular weight, thermodynamic compatibility, free volume, swelling ratio, constitutive model parameter or their combination.

In one embodiment, the cellulosic derivatives described herein are capable of forming gels of various strength, depending on their structure and concentration as well as, in another embodiment, environmental factors such as ionic strength, pH and temperature. The combined viscosity and gel behavior referred to as "viscoelasticity" in one embodiment, are examined by determining the effect that an oscillating force has on the movement of the material. In another embodiment elastic modulus (G'), viscous modulus (G"), and complex viscosity ($\eta^*$) are the parameters sought to be changed using the methods described herein, and these are analyzed in another embodiment by varying either stress or strain harmonically with time (Table 1). These parameters are derived from the complex modulus (G*), which is the ratio of maximum stress to maximum strain, and the phase angle ($\delta$), which is the angle that the stress and strain are out of phase.

TABLE 1

Relationships between dynamic moduli, phase angle ($\delta$), and frequency ($\omega$).

| Term | Symbol | Definition | Information provided |
| --- | --- | --- | --- |
| Complex modulus | G* | $[(G')^2 + (G'')^2]^{0.8}$ | All viscoelastic characteristics |
| Elastic modulus, storage modulus | G' | $G^* \cos \delta$ | Energy stored per deformation cycle; solid-like or elastic behavior |
| Viscous modulus, loss modulus | G" | $G^* \sin \delta$ | Energy dissipated per deformation cycle; gluid-like or viscous behavior |
| Complex viscosity | $\eta^*$ | $G^*/\omega$ | Viscoelastic flow |

In one embodiment, in the cellulosic derivatives described herein, some of the deformation caused by shear stress is elastic and will return to zero when the force is removed. The remaining deformation such as that deformation created by the sliding displacement of the chains through the solvent in one embodiment will not return to zero when the force is removed. Under a constant force the elastic displacement remains constant in one embodiment, whereas the sliding displacement continues, so increasing.

In one embodiment, the term "elastic," or "elasticity," and like terms refer to a physical property of the cellulosic derivative hydrogels described herein, namely the deformability of the hydrogel under mechanical force and the ability of the hydrogel to retain its original shape when the deforming force is removed. In another embodiment, the term "elastic modulus" refers to Young's Modulus and is a measure of the ratio of (a) the uniaxial stress along an axis of the material to (b) the accompanying normal strain along that axis.

The shear modulus (resulting from changing strain) is the ratio of the shear stress to the shear strain. It follows from the complex relationship similar to the above that:

$$G^*=G'+iG''$$

where G* is the complex shear modulus, G' is the in-phase storage modulus, i is a material-related factor and G" is the out-of-phase similarly-directed loss modulus; $G^*=E(G'2+G''2)$. The frequency where these parameters cross over corresponds to a relaxation time ($\tau$) specific for the material.

In one embodiment, linear viscoelastic properties of the cellulosic derivative hydrogels described herein are determined by measurements in an oscillating shear flow at small amplitude and with variable angular frequency. The values for G' and G" are determined to a great extent here by the concentration of the cellulose derivatives in the aqueous solution and the magnitude of the representative viscosity value. Therefore, hereinafter, only the relative course of G' and G" with increasing angular frequency $\omega$ is considered. In another embodiment, at a concentration of 1.5 to 2% (w/w) of cellulose derivative of aqueous solution and a temperature of approximately 20° C., the behaviour of G' and G" for the cellulose derivatives is such that at a low angular frequency (w), the storage modulus G' is less than the loss modulus G", but with increasing angular frequency G' increases more greatly than G". In another embodiment, G', above a certain angular frequency, finally becomes greater than G", and the solution at high values of angular frequency thus predominantly reacts elastically. This behavior is attenuated or changed using the crosslinking methods described herein.

In one embodiment, the term "Intrinsic viscosity ($[\eta^*]$) refers to the limit of the reduced viscosity extrapolated to zero concentration. As with the reduced viscosity, it has units of reciprocal concentration, for example, mL $g^{-1}$.

In one embodiment, the physico-chemical properties attenuated using the methods described herein, are further modified as a function of the polymer backbone degree of substitution, or hydrogel concentration, initial molecular weight of the cellulose derivative polymer, the cellulose derivative polymer type, crosslink density, photoinitiator concentration, electromagnetic radiation type, its wavelength exposure time and intensity, or their combination in other discrete embodiments.

In one embodiment, the polymer may also be crosslinked using redox initiators. Redox initiators refer in certain embodiments, to a mixture of two chemical agents that form free radicals capable of initiating polymerization of the hydrogel when in contact with each other. A commonly used water soluble redox initiator is a combination of ammonium persulfate (APS) and N,N,N',N'-tetramethylethylenediamine (TMED). The APS and TMED combination has been found to be biocompatible at various concentrations using cell monolayer cytotoxicity tests. Furthermore, studies have used this redox initiator for encapsulation of chondrocytes within a composite hydrogel. Other redox initiators utilizing a combination of persulfate oxidizing agents, APS and sodium persulfate, and ascorbic acid (AA) reducing agents, AA, sodium ascorbate, and magnesium ascorbate, have been studied for use in cell encapsulation applications.

In another embodiment, modification of methylcellulose is successful in producing stable, photocrosslinkable hydrogels for cell encapsulation. In another embodiment, the cells encapsulated in the attenuated hydrogels described herein remain evenly distributed throughout the construct and in another embodiment elaborated characteristic ECM components such as glycosaminoglycans (GAGs) and COL II, are retained by the hydrogel.

Methylcellulose offers in one embodiment, an FDA approved, cost-effective material with tunable properties for intradiscal replacement. In one embodiment, the swelling properties of the attenuated hydrogels provided herein allow for direct injection and in situ cross-linking at the injury site, with minimal bulging and extrusion to the annulus.

In one embodiment, the term "swelling index" refers to the free volume of the interior of a polymer, as a parameter for indicating the swelling degree of gel by solvent. The swelling index of the hydrogels used in the compositions and methods described herein, decreases as the cross-linking density increases, and it increases as the cross-linking density decreases. In another embodiment, the cross-linking density varies according to the amount of the cross-linkers charged thereto when the cellulosic hydrogels described herein are prepared, and impact resistance of the molded structure is improved in certain embodiments, as the swelling index is increased by the use of a small amount of the cross-linkers. In one embodiment, the degree of substitution of the crosslinker molecule used in the hydrogel structures described herein, is between about 1 and about 15%.

In another embodiment, the Example provided herein demonstrate an ability to synthesize and fabricate carboxymethylcellulose (CMC) hydrogels for encapsulation of cartilaginous tissue cells. In another embodiment, the CMC hydrogels present distinct advantages over existing materials used for engineering cartilaginous tissues, as these negatively-charged polysaccharides are similar to those found in native tissue and in one embodiment, provide an environment more conducive to swelling, nutrient transport and extracellular matrix organization in comparison to inert polymers, such as polyethylene oxide. In one embodiment, CMC is more cost-effective than other polysaccharides (i.e., chondroitin sulfate and hyaluronic acid) currently used for similar applications.

In one embodiment, the step of forming a hydrogel from the substituted cellulose derivative polymer in the cellulosic derivative hydrogels described herein, is preceded by a step of solubilizing the substituted polymer backbone and suspending in the solubilized polymer, a composition comprising a cell type, for which growth is sought. In another embodiment, the cell is a stem cell, a dendritic cell, a mesenchymal stem cell, a nucleus pulposus cell, a progenitor cell, a dermis-derived fibroblastic cell, a cartilaginous tissue cell or their combination.

In one embodiment, the stem cell whose growth is sought may be a somatic stem cell or an embryonic stem cell, a human stem cell or an animal stem cell, and includes a somatic mesenchymal stem cell (MSC). Examples of MSCs that can be grown using the cellulosic derivative hydrogels described herein, include bone marrow-derived MSCs, renal MSCs, hepatic-derived MSCs, adipose-derived MSCs, skeletal muscle-derived MSCs, bone-derived MSCs, dental pulp MSCs, cardiac muscle-derived MSCs, synovial fluid-derived MSCs, and umbilical cord MSCs. Other types of cells that can be grown in the cellulosic derivative hydrogels described herein using a method of the present invention will be apparent to those of skill in the art in light of this specification.

"Stem cell" means a cell that is able to self-renew by proliferation and to differentiate into multiple distinct cell types. "Somatic stem cell" means a non-embryonic (i.e., adult) stem cell.

Stem cells, including mesenchymal stem cells, used or useful in methods of the invention may be harvested from living tissue such as bone marrow. For example, bone marrow aspirated from a living donor can be pipetted onto a commercially available glass or plastic tissue culture plate with undisclosed surface coating by manufacturers. (E.g., A. J. Friedenstein, U. Gorskaja, N. N. Kulagina, Exp. Hematol. 4, 276 (1976).) It has been found that bone marrow MSCs adhere to the coated glass, for example, while other types of bone marrow cells do not.

In one embodiment, the term "nucleus pulposus" refers to the central zone of the intervertebral disc, which is gel-like and has a similar collagen phenotype to that of hyaline cartilage. In another embodiment, articular cartilage covers the ends of bones in diarthroidial joints in order to distribute the forces of locomotion to underlying bone structures while simultaneously providing nearly frictionless articulating interfaces. These properties are furnished by the extracellular matrix composed of type II collagen and other minor collagen components and a high content of the proteoglycan aggrecan. In one embodiment, the fibrillar collagenous network resists tensile and shear forces while the highly charged aggrecan resists compression and interstitial fluid flow. The low friction properties are the result of a special molecular composition of the articular surface and of the synovial fluid as well as exudation of interstitial fluid during loading onto the articular surface. In one embodiment, changing the physico-chemical properties of the cellulose-derived hydrogels described herein, allows for the replacement of articular cartilage, or its regeneration in another embodiment.

In one embodiment, the composition used in the cellulosic derivative hydrogels described herein, further comprises peptides, morphogens, growth factors, hormones, small molecules, and cytokines. Examples include insulin-like-growth factors transforming growth factors, polylactic acid (PLA), polyglycolic acid (PGA), bone morphogenetic proteins, angiotensin-like peptides, mixtures of collagen, chitosan and glycosaminoglycans, a crushed cartilage and bone paste.

In one embodiment, the term "volume of interest" (VOI) refers to a site, in or on which the implant is formed or applied, as for example, a soft tissue such as muscle or fat. Embodiments of implant VOI include a tissue defect such as a tissue regeneration site; a void space such as a periodontal pocket, surgical incision or other formed pocket or cavity; a natural cavity such as the oral, vaginal, rectal or nasal cavities, the cul-de-sac of the eye, and the like; and other VOI into which the implant comprising the biomaterials described herein may be placed and formed into a solid implant.

In one embodiment, provided herein is a method of making an implant for the reconstruction, repair or augmentation of a soft tissue in a subject, comprising the step of: identifying a volume of interest to be repaired, reconstructed or augmented in the subject; filling the volume with a biomaterial, the biomaterial comprising a methacrylate-substituted cellulose derivative polymer, wherein the methacrylate-substituted cellulose derivative polymer is photocrosslinkable or redox-crosslinkable; in the presence of a photoinitiator, crosslinking the polymer; and forming a hydrogel.

Suitable biologically-active agents for use in the biomaterial compositions, methods and kits described herein also include anti-inflammatory agents such as hydrocortisone, prednisone and the like; anti-bacterial agents such as penicillin, cephalosporins, bacitracin and the like; antiparasitic agents such as quinacrine, chloroquine and the like; antifungal agents such as nystatin, gentamicin, and the like; antiviral agents such as acyclovir, ribarivin, interferons and the like; antineoplastic agents such as methotrexate, 5-fluorouracil, adriamycin, tumor-specific antibodies conjugated to toxins, tumor necrosis factor, and the like; analgesic agents such as salicylic acid, acetaminophen, ibuprofen, flurbiprofen, morphine and the like; local anaesthetics such as lidocaine, bupivacaine, benzocaine and the like; vaccines such as hepatitis, influenza, measles, rubella, tetanus, polio, rabies and the like; central nervous system agents such as a tranquilizer, B-adrenergic blocking agent, dopamine and the like; growth factors such as colony stimulating factor, platelet-derived growth factor, fibroblast growth factor, transforming growth factor B, human growth hormone, bone morphogenetic protein, insulin-like growth factor and the like; hormones such as progesterone, follicle stimulating hormone, insulin, somatotropins and the like; antihistamines such as diphenhydramine, chlorphencramine and the like; cardiovascular agents such as digitalis, nitroglycerine, papaverine, streptokinase and the like; anti-ulcer agents such as cimetidine hydrochloride, isopropamide iodide, and the like; bronchodilators such as metaproternal sulfate, aminophylline and the like; vasodilators such as theophylline, niacin, minoxidil, and the like; and other like substances.

The crosslinkable cellulose derivative polymer comprises monomers and/or oligomers having polymerizable groups, which crosslink to form a polymer network. Suitable polymerizable groups include unsaturated alkenes (i.e., vinyl groups) such as vinyl ethers, allyl groups, unsaturated monocarboxylic acids, unsaturated dicarboxylic acids, and unsaturated tricarboxylic acids. Unsaturated monocarboxylic acids include acrylic acid, methacrylic acid and crotonic acid. Unsaturated dicarboxylic acids include maleic, fumaric, itaconic, mesaconic or citraconic acid. In certain embodiments, the polymerizable groups are acrylates, diacrylates, oligoacrylates, dimethacrylates, oligomethacrylates, and other biologically acceptable polymerizable groups.

In one embodiment, the biomaterial compositions used in the implants described herein further comprises an initiator, such as a photoinitiator in one embodiment or a combination of a photoinitiator and a redox initiator system in another embodiment.

In one embodiment, the biomaterial compositions contain free-radical initiators such as photoinitiators, thermally activated initiators, redox initiator systems, ionic initiators or mixture thereof. Any free-radical initiators or combination of initiators can be used. In another embodiment, one or more photoinitiator(s) is used. In one embodiment, one or more redox initiator system(s) is used. In another embodiment, one or more photoinitiator(s) is used in combination with one or more redox initiator system(s).

A redox initiator system includes an oxidizing agent (also called an oxidizing component) (such as a peroxide) and a reducing agent (also called a reducing component) (such as an aromatic or aliphatic amine). Combining the redox couple results in the generation of an initiating species (such as free radicals or cations) capable of causing crosslinking. Preferably, the redox couples of this invention are activated at temperatures below about 40° C., for example, at room temperature or at the physiological temperature of about 37° C.

Generally, the redox couple is partitioned into separate reactive compositions prior to use and then subsequently mixed at the time of use to generate the desired initiating species. Selection of the redox couple is governed by several criteria. For example, a desirable oxidizing agent is one that is sufficiently oxidizing in nature to oxidize the reducing agent, but not excessively oxidizing that it may prematurely react with other components with which it may be combined during storage. Similarly, a desirable reducing agent is one that is sufficiently reducing in nature to readily react with the preferred oxidizing agent, but not excessively reducing in nature such that it may reduce other components with which it may be combined during storage. Oxidation or reduction of the resin with an inappropriate reducing agent or oxidizing agent, respectively, could result in an unstable system that would prematurely polymerize and subsequently provide a limited shelf life. Thus, suitable redox couples individually provide good shelf-life (for example, at least 2 months, preferably at least 4 months, and more preferably at least 6 months in an environment of 5-20° C.), and then, when combined together, generate the desired initiating species for crosslinking or partially crosslinking the curable admixture.

Suitable oxidizing agents include peroxide compounds (i.e., peroxy compounds), including hydrogen peroxide as well as inorganic and organic peroxide compounds (e.g., "per" compounds or salts with peroxoanions). Examples of suitable oxidizing agents include, but are not limited to: peroxides such as benzoyl peroxide, phthaloyl peroxide, substituted benzoyl peroxides, acetyl peroxide, caproyl peroxide, lauroyl peroxide, cinnamoyl peroxide, acetyl benzoyl peroxide, methyl ethyl ketone peroxide, sodium peroxide, hydrogen peroxide, di-tert butyl peroxide, tetraline peroxide, urea peroxide, and cumene peroxide; hydroperoxides such as p-methane hydroperoxide, di-isopropyl-benzene hydroperoxide, tert-butyl hydroperoxide, methyl ethyl ketone hydroperoxide, and 1-hydroxy cyclohexyl hydroperoxide-1, ammonium persulfate, sodium perborate, sodium perchlorate, potassium persulfate, etc.; ozone, ozonides, etc. These oxidizing agents may be used alone or in admixture with one another. Benzoyl peroxide is the preferred oxidizing agent. One or more oxidizing agents may be present in an amount sufficient to provide initiation of the curing process. Preferably, this includes about 0.01 weight percent (wt-%) to about 4.0 wt-%, and more preferably about 0.05 wt-% to about 1.0 wt-%, based on the total weight of all components of the dental material.

A reducing agent has one or more functional groups for activation of the oxidizing agent. Preferably, such functional group(s) is selected from amines, mercaptans, or mixtures thereof. If more than one functional group is present, they may be part of the same compound or provided by different compounds. A preferred reducing agent is a tertiary aromatic amine (e.g., N,N-dimethyl-p-toluidine (DMPT) or N,N-bis (2-hydroxyethyl)-p-toluidine (DHEPT)). Examples of such tertiary amines are well known in the art and can be found, for example, at WO 97/35916 and U.S. Pat. No. 6,624,211. Another preferred reducing agent is a mercaptan, which can include aromatic and/or aliphatic groups, and optionally polymerizable groups. Preferred mercaptans have a molecular weight greater than about 200 as these mercaptans have less intense odor. Other reducing agents, such as sulfinic acids, formic acid, ascorbic acid, hydrazines, and salts thereof, can also be used herein to initiate free radical polymerization.

In one embodiment, the implant composition described herein include a biologically active agent in mixture with a moldable, pliable solid formed from the methacrylate-substituted cellulose derivative polymer, wherein the methacrylate-substituted cellulose derivative polymer is photocrosslinkable or redox-crosslinkable. In another embodiment, the implant composition can be prepared by any combination of steps in which the aqueous medium is added to a mixture of biomaterial compositions described herein, hereinafter termed "flowable composition", and the biologically active agent is present either in the flowable composition or the aqueous medium.

In another embodiment, the molecules comprising the cellulosic derivative hydrogels described herein, is adhesion peptides from ECM molecules, laminin peptides, fibronectin peptides, collagen peptides, heparin sulfate proteoglycan binding peptides, Hedgehog, Sonic Hedgehog (Shh), Wnt, bone morphogenetic proteins, Notch (1-4) ligands, Delta-like ligand 1, 3, and 4, Serrate/Jagged ligands 1 and 2, fibroblast growth factor, epidermal growth factor, platelet derived growth factor, transforming growth factor-$\beta1$, -$\beta2$, and $\beta3$, Eph/Ephrin, Insulin, Insulin-like growth factor, vascular endothelial growth factor, neurotrophins, BDNF, NGF, NT-3/4, retinoic acid, forskolin, purmorphamine, dexamethasone, 17.beta.-estradiol and metabolites thereof, 2-methoxyestradiol, cardiogenol, stem cell factor, granulocyte-macrophage colony-stimulating factor, granulocyte colony-stimulating factor, interleukins, IL-6, IL-10, -11, cytokines, Flt3-1, Leukaemia inhibitory factor, transferrin, intercellular adhesion molecules, ICAM-1 (CD54), VCAM, NCAM, tumor necrosis factor alpha, HER-2, and stromal cell-derived factor-1 alpha.

In one embodiment, provided herein is a method of modifying a physico-chemical property of a cellulose derivative polymer hydrogel comprising the step of covalently substituting an unprotected group on the cellulose derivative polymer backbone with photocrosslinkable groups, or redox-crosslinkable groups, forming a hydrogel from the substituted cellulose derivative polymer; and cross-linking the hydrogel, whereby the step of substituting an unprotected group on the cellulose derivative polymer backbone with photocrosslinkable groups is done via esterification of hydroxyl groups using methacrylic anhydride. In one embodiment, the degree of substitution is between about 1 and about 15%.

In one embodiment, photopolymerization is an effective method of generating mechanically stable hydrogels through the introduction of covalent bonds between polymer chains. In another embodiment, MC is successfully modified in an aqueous environment incorporating functional methacrylate groups onto the polymer backbone, which undergoes free radical polymerization in the presence of a photoinitiator and upon exposure to UV light. In other embodiments, these hydrogels are easily fabricated at varying weight percentages, demonstrating tunable material properties and are well tolerated in vitro and in vivo.

In one embodiment, the degree of substitution of the crosslinking agent that is covalently attached to the cellulose derivative in the cellulose derivative hydrogels which physico-chemical properties were attenuated using the methods described herein, is between about 1 and about 15%.

In one embodiment, the electromagnetic radiation used to initiate the crosslinking used to modify the physico-chemical properties as a function of electromagnetic radiation type, its wavelength exposure time and intensity, or their combination, is UV light. In another embodiment, the exposure is between about 1 and 15 minutes.

In another embodiment, the hydrogel concentration used in the method of modifying a physico-chemical property of a cellulose derivative polymer hydrogel is between about 1 and 15% (w/v). In another embodiment, the hydrogel concentration is between 1 and 3%, or between about 3 and 6% (w/v) in another embodiment. In another embodiment, the hydrogel concentration is between 6 and 9%, or between about 9 and 12% (w/v) in another embodiment. In another embodiment, the hydrogel concentration is between 12 and 14%, or between about 12 and 15% (w/v) in another embodiment.

In one embodiment, whereby the initial molecular weight of the cellulose derivative polymer used in the method of modifying a physico-chemical property of a cellulose derivative polymer hydrogel is between about 10 and 1000 kDa. In one embodiment, the initial molecular weight of the cellulose derivative polymer is between about 10 and 1000 kDa, or between 10 and 100 kDa in another embodiment. In one embodiment, the initial molecular weight of the cellulose derivative polymer is between about 100 and 200 kDa, or between 200 and 400 kDa in another embodiment. In one embodiment, the initial molecular weight of the cellulose derivative polymer is between about 400 and 600 kDa, or between 600 and 800 kDa in another embodiment. In one embodiment, the initial molecular weight of the cellulose derivative polymer is between about 800 and 900 kDa, or between 900 and 1000 kDa in another embodiment.

In one embodiment, methylcellulose was modified in order to produce photopolymerizable MC hydrogels. The material properties (i.e., swelling ratio, modulus) of photocrosslinked MC hydrogels were evaluated as were the cytotoxicity and biocompatibility of the materials in vitro and in vivo are described. In another embodiment, increasing weight percentages of MC hydrogels demonstrates a lower swelling ratio and greater compressive moduli and exhibit low cytotoxicity with a minimal inflammatory response in vivo, making it a novel filler for soft tissue reconstruction, as well as other various applications. In one embodiment, the viability of human dermal fibroblasts exposed to freshly cast MA-MC hydrogels was not significantly affected, showing that the hydrogels used in the compositions, methods and kits described herein are non-cytotoxic and biocompatible.

In another embodiment, hydrogels formulated with a higher weight percentage of MA-MC exhibit greater compressive moduli in comparison to lower weight percentage hydrogels. Despite a three-fold increase in stiffness from 4 wt % to 6 wt % hydrogels, as measured by Young's modulus in one embodiment, there is less than a 10% reduction in the swelling ratio. Higher weight percentage hydrogels contain a larger concentration of methacrylated polymer chains. Upon polymerization, they exhibit a greater degree of crosslinking, resulting in a more densely packed polymer network. This increase in crosslinking density decreases the critical segment length of polymer backbone and minimizes swelling in aqueous environments, giving rise to higher compressive moduli. In one embodiment, water movement reaches equilibrium within 30 minutes for all MA-MC formulations, with small changes in hydrogel diameter. Maintaining a constant swelling ratio over time is particularly useful in another embodiment, for applications in which hydrogel geometry must be maintained, such as in reconstructive surgery in one embodiment.

Figure 8:
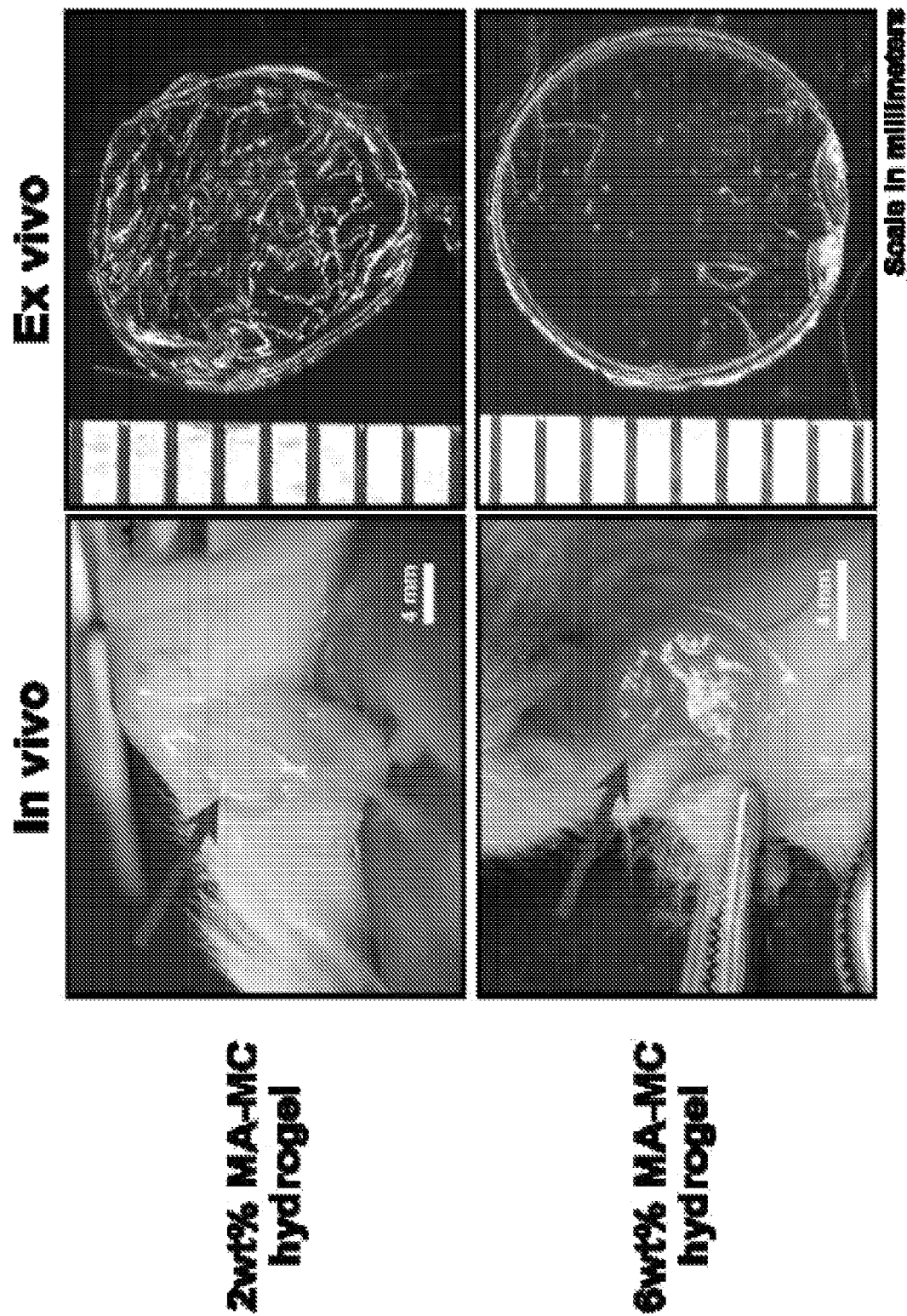
FIG. 8 shows representative gross images of a 2 wt % and 6 wt % MC-MA hydrogels (indicated with arrows) 7 days after implantation subcutaneously in CD1 mice both in vivo and ex vivo.
Figure 10:
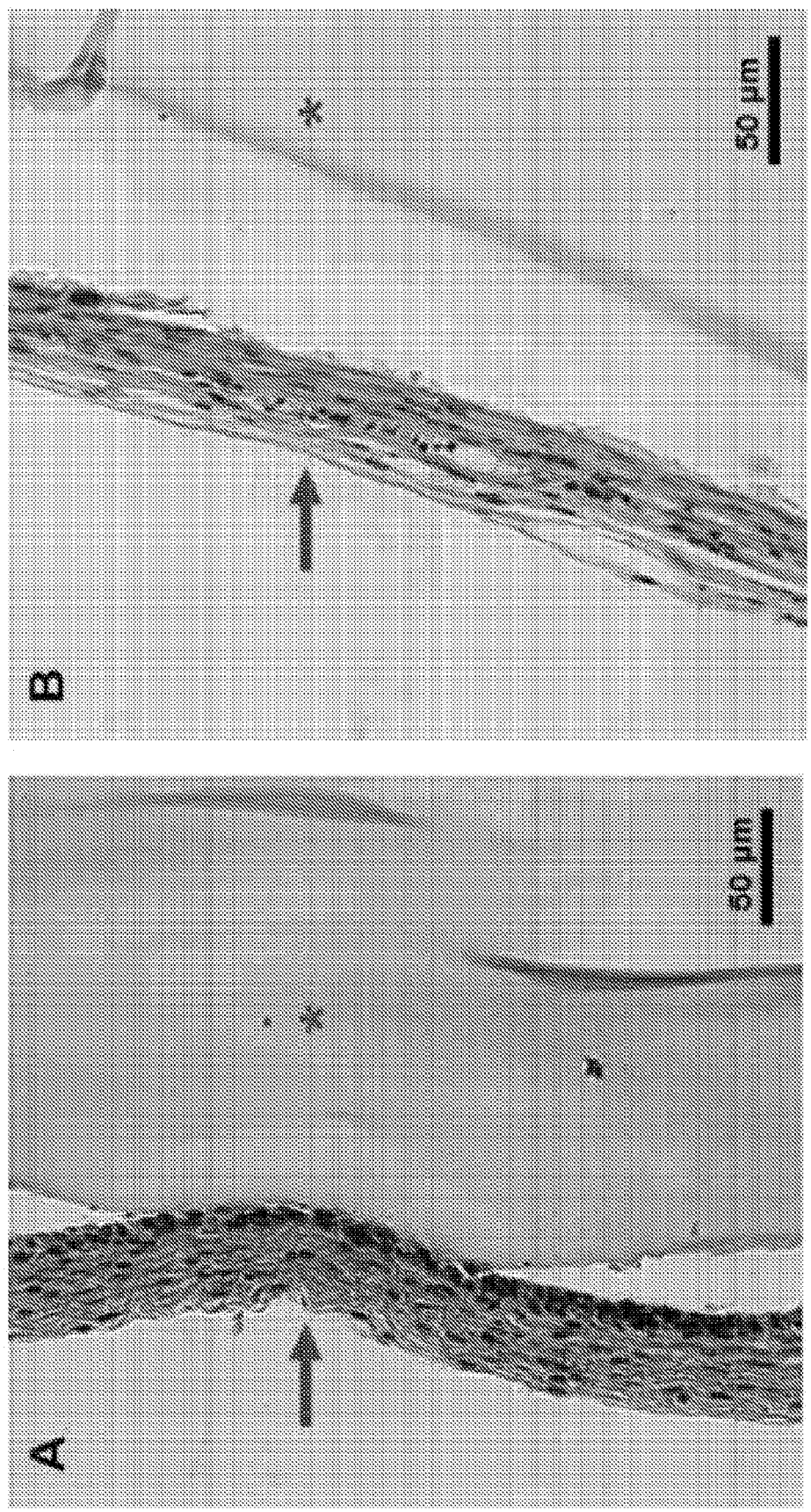
FIG. 10 shows representative images of hematoxylin and eosin stained 6 wt % MC-MA hydrogels (indicated with an asterisk) within the fibrous capsule (indicated with an arrow). (A) 30 days and (B) 80 days after implantation subcutaneously in CD1 mice.

Surprisingly, in one embodiment, 2 wt % hydrogels break down after 30 days in vivo but remain intact at higher weight percentage (6 wt %) with minimal degradation. FIG. 8 shows an intact 2 wt % MA-MC hydrogel after 7 days in vivo that appears deformed once excised. After 30 days, however, 2 wt % gels are dissociated into unrecoverable small fragments. In another embodiment, 2 wt % hydrogels are non-degradable, but are too weak to withstand the mechanical stresses of implantation and normal tissue activity of a mobile subject. This is supported by the lower mechanical strength of 2 wt % MA-MC hydrogels. At all time points 2 wt % and 6 wt % MA-MC hydrogels exhibit only a minimal inflammatory response. Excised samples are circumscribed in one embodiment, by a thin translucent capsule with no inflammatory exudates even after 80 days in vivo. Histological evaluation of 80-day implants reveals in another embodiment, a 50 nm loosely organized fibrous capsule comparable in thickness to the denser capsule present at 30 days (FIG. 10). This inflammatory response is mild when compared to other characterized biomaterials. In one embodiment, when implanted subcutaneously in normal rats, poly(glycolic acid) generates a fibrous capsules approximately 450 nm in thickness, after only 5 days, which consist of dense granulation tissue with significant cell infiltration. In one embodiment, a dextranbased hydrogel system elicits a mild inflammatory response when implanted intramuscularly, resulting in the formation of a thin fibrous capsule (<55 nm in thickness) that contains macrophages and giant cells.

Dermal implants and injectable fillers are used in one embodiment, to augment normal tissue architecture often depleted by loss of dermal collagens and subcutaneous fat as a result of disease, trauma and natural aging.

In one embodiment, provided herein is method of reconstructing, repairing or augmenting a soft tissue in a subject in need thereof, comprising the step of implanting in an affected area of the soft tissue a biomaterial comprising a methacrylate-substituted cellulose derivative polymer, wherein the methacrylate-substituted cellulose derivative polymer is photocrosslinkable or redox-crosslinkable; in the presence of a photoinitiator, crosslinking the polymer; and forming a hydrogel.

The volume augmentation methods and kits described herein are intended to be used in one embodiment, for tissue bulking in a variety of circumstances, depending on the need. In one embodiment in gastroenterology, wherein increasing the volume of tissue at the gastro-esophageal junction is used to treat gastro-esophageal reflux disease, and increasing the thickness of the gastric mucosa to decrease the volume of the stomach to treat morbid obesity. In another embodiment; in urology, where placing filler radially around the urethra at the neck of the urinary bladder ameliorates incontinence. In another embodiment, in cardiology, whereby tissue filler is placed in the ventricular wall to decrease the volume of the left ventricular chamber to treat heart failure, or in another embodiment, in the pericardial space to place pressure on the outside of the heart, also intended to decrease the volume of the heart chambers and thereby treat heart failure. In other embodiments, the methods compositions and kits described herein are used in other applications well known to those skilled in the art. In any of these clinical applications, the tissue-filling compositions may be combined with any number of other bioactive substances which may be released from the filler itself over time, or be injected concurrently.

It will be readily understood to a person of ordinary skill in the art that the mechanical requirements of each embodiment of the applications described herein will differ in the physicochemical characteristics of the resulting filler, in terms of G', G", tan-d, Young's modulus, glass transition temperature, inherent viscosity, effective molecular weight, thermodynamic compatibility, free volume, swelling ratio, constitutive model parameter and their combination.

In one embodiment, Breast-conserving therapy (BCT), consisting of lumpectomy followed by radiotherapy, has become the standard form of treatment for invasive breast carcinomas up to 4 cm and 5 cm and is increasingly being used for ductal carcinoma in situ (DCIS) and larger tumors. In one embodiment, with BCT for large tumors, there is a difficulty in obtaining clear excision margins, and the cosmetic outcome is often poor. The tumor size in relation to the breast size is one of the most important factors when attempting to obtain a cosmetically favorable result. In another embodiment, there is a conflict between performing a resection wide enough to obtain optimal oncologic control and not removing so much breast tissue as to leave a deformed breast or a large discrepancy compared with the other side. In one embodiment, the compositions described herein resolve this dilemma by allowing for remodeling mammaplasty to reshape the breast immediately following lumpectomy. Accordingly, in one embodiment, following lumpectomy whereby a resection wide enough to obtain optimal oncologic control is carried out, followed by radiotherapy, the resected area is filled with the compositions described herein creating a natural mold; and is converted to an in-situ implant.

In another embodiment, provided herein is a method of smoothing skin wrinkles in a subject, comprising the steps of: injecting into a skin wrinkle a composition comprising a methacrylate-substituted cellulose derivative polymer, wherein the methacrylate-substituted cellulose derivative polymer is photocrosslinkable or redox-crosslinkable; filling the wrinkle; and exposing the skin to an electromagnetic radiation source, thereby forming a crosslinked hydrogel in-situ.

In one embodiment, provided herein is a kit for smoothing skin wrinkles in a subject, comprising a composition, the composition comprising an injectible polymer suspension wherein the polymer suspension comprises a methacrylate-substituted cellulose derivative polymer photocrosslinkable or redox-crosslinkable; a needle that is adapted for insertion under the surface of the skin, a plurality of syringes that hold the composition; an electromagnetic radiation source; and instructions The present description of a cellulose-based photopolymerizable hydrogel system utilizes MC, as the simplest derivative of cellulose. In one embodiment, the cellulose-based hydrogels are further optimized for biomedical applications. In another embodiment, the Cellulose derivatives used in the methods, kits and compositions described herein undergo further chemical modification yielding other derivatives such as hydroxypropylcellulose, carboxymethylcellulose or hydroxypropylmethylcellulose. These derivatives, which differ in their substituents which have various affinities to water and can impact in other embodiments, the swelling of the resulting hydrogel. To fabricate stiffer hydrogels, the molecular weight of the starting material in one embodiment, or the degree of substitution on the cellulose backbone in another, can be increased, resulting in more functional groups available to form crosslinks upon polymerization. In one embodiment, composite mixtures of various cellulose-based derivatives are also useful. In one embodiment, the biological and material properties of MA-MC hydrogels described in the methods, kits and compositions described herein, provide a foundation for the development of cellulose-based photopolymerizable hydrogels for applications ranging from dermal fillers to drug delivery and cell encapsulation.

In one embodiment, the MC macropolymer used in the biomaterial compositions, methods and kits described herein is modified through co-polymerization with dextran, thereby leading to a dextran-methylcellulose copolymer, which in another embodiment can undergo degradation in the body via contact with dextranase, making any hydrogel filler, a semi-permanent filler.

In another embodiment, the biomaterials described herein further comprise an encapsulant integrated into the hydrogel matrix. The encapsulant used in the biomaterial compositions, methods and kits described herein is an application specific encapsulant. Accordingly, in one embodiment, the desired application is a filler for age related wrinkles. Encapsulant used is in one embodiment a botulism toxin, or a tetrodotoxin, an analgesic, an anti-inflammatory, or their combination in other embodiment. In one embodiment, initial polymer concentration polymer weight, and degree of substitution are adjusted to obtain the desired viscosity for injection of the material in the form of a microdispersion. The viscosity of the microdispersion comprising the polymer substituted with a photopolymerizable group and the encapsulants described herein, may also vary depending on the relative amounts of the fluid carrier and the particulate material comprising the encapsulants in the microdispersion as well as on the composition of the liquid polymeric carrier and the type of particulate material. In one embodiment, the shear viscosity of the microdispersion will be less than 1000 Pascal seconds (10,000 poise) and in another embodiment in the range of between about 2 Pa·s (20 poise) and 200 Pa·s (2,000 poise) as determined by capillary rheometry in certain embodiments.

Botulinum toxin is used in one embodiment to paralyze the small facial muscles around dynamic wrinkles in the forehead and around the eyes. In another embodiment, the substituted polymer described herein, is used to smooth non-dynamic wrinkles or augment facial tissues (nasolabial lines, lips, etc.).

In one embodiment, the hydrogels used in the biomaterial compositions, methods and kits described herein are used in the repair, reconstruction or augmentation of soft tissue, such as soft tissue defects in one embodiment, or contour abnormalities caused by a variety of factors, such as facial defects, acne, surgical scarring or aging, accidents or purely for cosmetic reasons. In certain embodiments, the hydrogels may be for uses in correction of facial contour deformities due to ageing, acne, trauma, surgery, infection or congenital deformities. The facial features in need of correction are in another embodiment, the cheekbones, nasolabial folds, glabellar frowns, depressed contours of the mouth, the chin, the size or shape the lips, as well as other soft tissue deficiencies of the face in other discrete embodiments. In another embodiment, the hydrogel used in the biomaterial compositions, methods and kits described, restores the skin contours correcting soft tissue contour deformities of the face such as wrinkles and folds.

The term "about" as used herein means in quantitative terms plus or minus 5%, or in another embodiment plus or minus 10%, or in another embodiment plus or minus 15%, or in another embodiment plus or minus 20%.

The following examples are presented in order to more fully illustrate the preferred embodiments of the invention. They should in no way be construed, however, as limiting the broad scope of the invention.

EXAMPLES

Example 1

Figure 2:
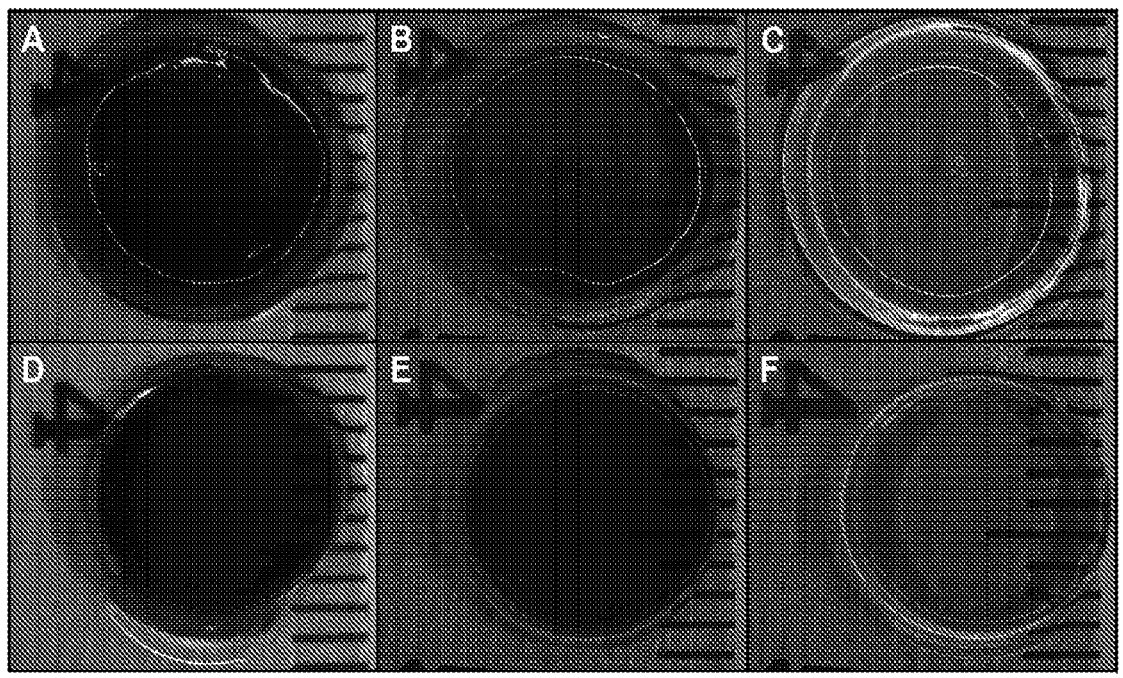
FIG. 2 shows a stereomicrograph following MTT incubation of 2% (A-C) and 3% (D-F) methylcellulose (MC) gels at day 7 (A,D) and day 14 (B,E) and no-cell controls (C,F). Scale in mm.
Figure 3:
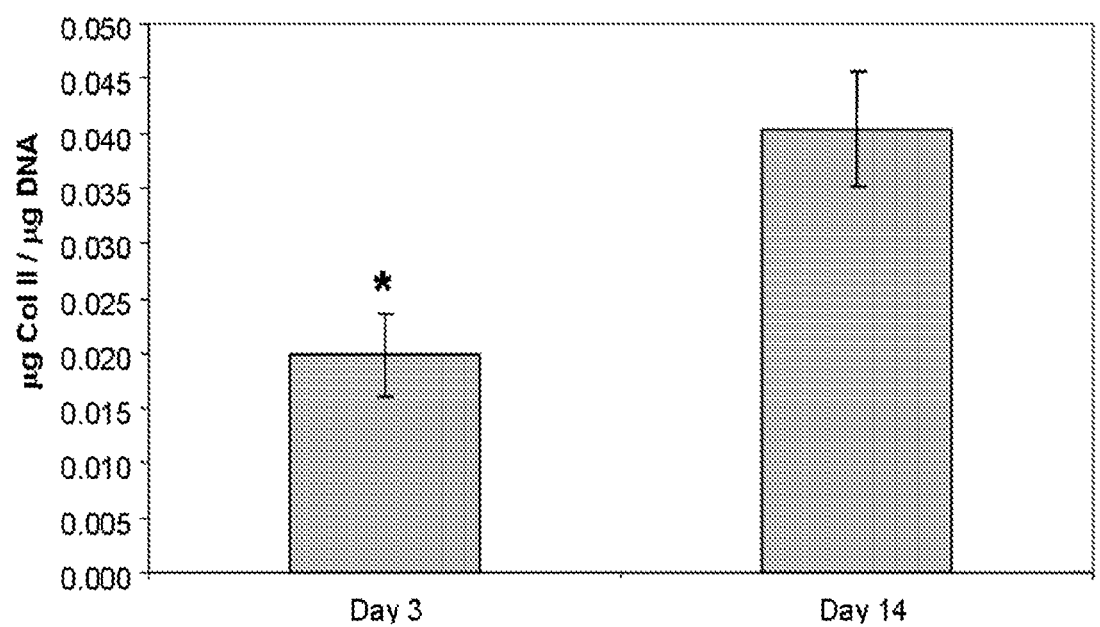
FIG. 3 shows normalized type II collagen (COL II) ELISA of 3% methylcellulose gels. * indicates significance vs. day 14.

Development of Photocrosslinked Methylcellulose Hydrogels Encapsulated with Nucleus Pulposus Cells Methylcellulose was modified with methacrylate groups and photocrosslinked to form stable hydrogels. The average diameter of 2% gels was significantly greater than that of 3% gels (8.43±0.21 vs. 7.98±0.14 mm, respectively). Although viability decreased over time, viable cells were evenly distributed throughout the constructs at days 7 and 14 (FIG. 2). Safranin-O staining indicated the presence of GAGs diffused throughout the gel in 2% scaffolds while staining in 3% gels was localized to cells. Further evaluation of 3% gels demonstrated a significant increase in normalized COL II production over 14 days (FIG. 3).

Figure 4:
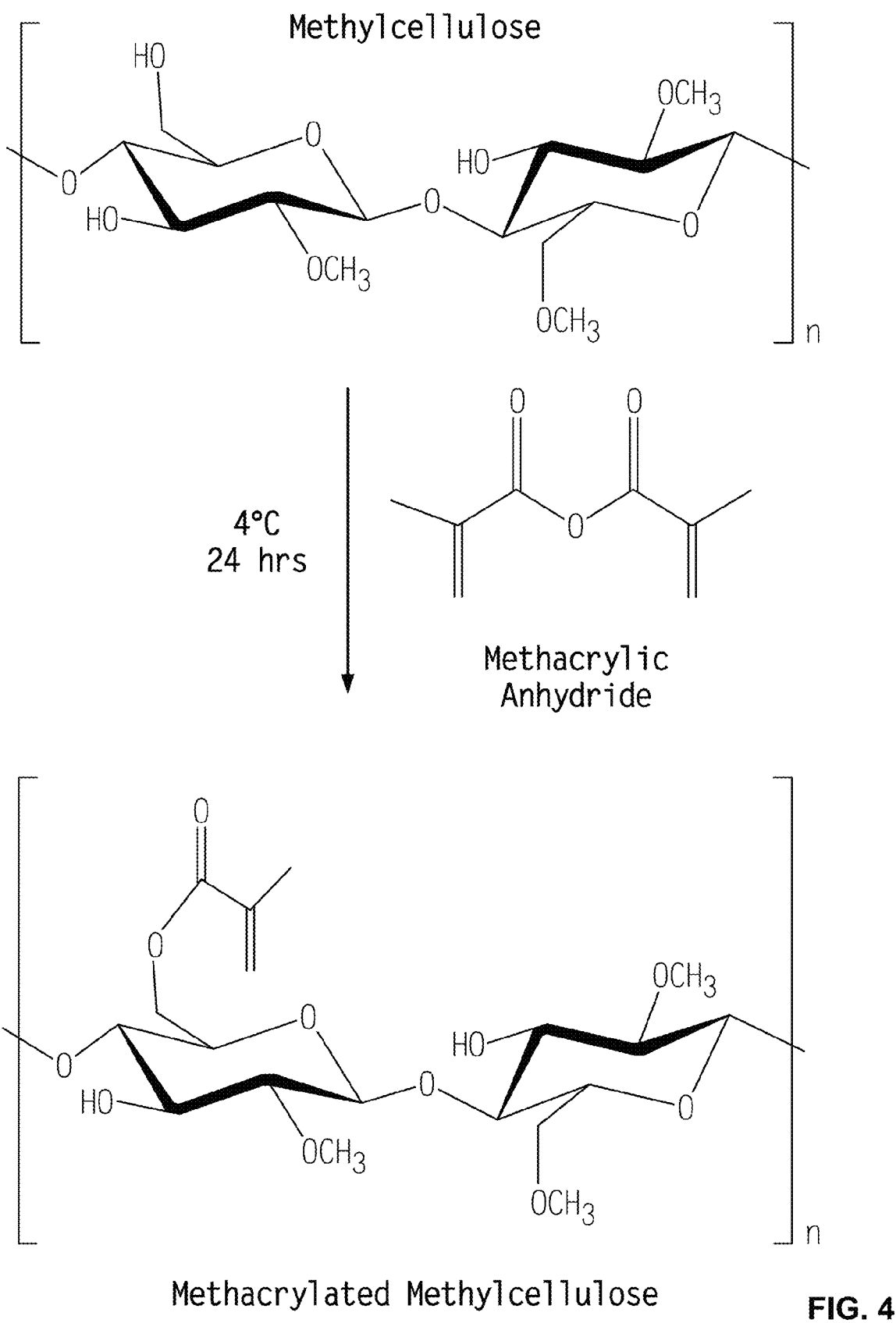
FIG. 4 shows a schematic of the synthesis of methacrylated methylcellulose (MA-MC)

Comparable viability was measured for both 2 and 3% gels; however 3% gels allowed for greater ease of handling.
Primary Cell Isolation NP cells were isolated from bovine caudal IVDs by collagenase digestion and designated as passage 0.
Macromer Synthesis Methacrylated methylcellulose (MA-MC) was synthesized through esterification of hydroxyl groups based on previously described protocols (FIG. 4). Briefly, 1 gram of 15 kDa MC (Sigma, St. Louis, Mo.) was dissolved in 35 mL of sterile water at a temperature of 80° C. To this solution, 65 mL of sterile water at 4° C. was added and stirred f or 30 minutes yielding a 1 wt % MC solution. A 5% theoretically modified solution of MC was prepared by reacting methacrylic anhydride (Sigma, St. Louis, Mo.) in 20-fold excess to the 1 wt % MC over 24 hours at 4° C. with periodic adjustments to pH 8.0 using 3N NaOH (approximately 12 times over the course of the reaction). The modified MC solution was purified via dialysis for at least 48 hours against sterile water (Spectra/Por 1, MW 5-8 kDa, Rancho Dominguez, Calif.) to remove excess methacrylic anhydride and the final product was recovered by lyophilization. Methacrylation was confirmed using $^1$H-NMR. Purified MA-MC was recovered by lyophilization and stored at −20° C.
NMR Analysis 1H-NMR (360 MHz, DMX360, Bruker, Madison, Wis.) was performed on acid hydrolyzed MA-MC to confirm the degree of substitution of purified MA-MC. Briefly, a 20-mg sample of lyophilized MA-MC was dissolved in 20 mL of sterile water and underwent acid hydrolysis at a pH of 2.0 at 80° C. for 2 hours. The pH of the hydrolyzed solution was re-adjusted to 7.0, recovered via lyophilization and resuspended in $D_2O$. Molar percent of methacrylation was determined by the relative integrations of the methacrylate proton peaks (methylene, δ=6.0 ppm and 5.6 ppm and the methyl peak, δ=1.8 ppm) to carbohydrate protons.
Hydrogel Preparation for Cell Encapsulation $10 \times 10^6$ cells/mL were encapsulated in 2 and 3% (w/v) UV-sterilized methacrylated methylcellulose dissolved in 0.05% 12959 photoinitiator (IRGACURE® 2959, Ciba Specialty Chemicals) through exposure to long wave UV light for 10 minutes. A custom-made casting device was used to produce disks of 8-mm diameter×2-mm thickness.
Cell Culture Passage 2 cells were used in all studies. Cultures were incubated at 37° C., 5% $CO_2$ and in DMEM supplemented with 10% FBS, 50 µg/mL L-ascorbic acid, and antibiotics. Medium was replaced every 2 days. Cultures were analyzed for viability and glycosaminoglycan (GAG) and type II collagen (COL II) production over 14 days.
Cell Isolation All cell culture supplies, including media, antibiotics, and buffering agents, were purchased from Invitrogen (Carlsbad, Calif.) unless otherwise noted. Discs C2-C4 were isolated from bovine caudal IVDs obtained from a local abattoir, and the NP was separated through gross visual inspection based on previous protocols. Tissue was maintained in Dulbecco's Modified Eagle Medium (DMEM) supplemented with 20% fetal bovine serum (FBS) (Hyclone, Logan, Utah), 0.075% sodium bicarbonate, 100 U/mL penicillin, 100 µg/mL streptomycin, and 0.25 µg/mL Fungizone reagent at 37° C., 5% CO2 for two days prior to digestion to ensure no contamination occurred during harvesting. A single serum lot was used for all experiments to reduce potential variability in the cellular response.

Tissue was diced and NP cells were released by collagenase (Type IV, Sigma) digestion at an activity of 7000 U collagenase per gram of tissue. Following incubation in collagenase, undigested tissue was removed using a 40 µm mesh filter. Cells from multiple levels (C2-C4) were pooled and rinsed in sterile Dulbecco's Phosphate Buffered Saline (DPBS). These primary cells were plated onto tissue culture flasks and designated as passage 0. Cells were subcultured twice to obtain the necessary number of cells, and passage 2 cells were used in all experiments.
Cell Encapsulation in Photocrosslinked Hydrogels Cell-encapsulated photocrosslinked constructs were prepared at various weight percents. Prior to dissolution, lyophilized Me-CMC was sterilized by a 30-minute exposure to germicidal UV light. The sterilized product was then dissolved in filter-sterilized 0.05 wt % photoinitiator, 2-methyl-1-[4-(hydroxyethoxy)phenyl]-2-methyl-1-propanone (IRGACURE® 2959, 12959, Ciba Specialty Chemicals, Basel, Switzerland), in sterile DPBS at 4° C. to various weight percents (90 kDa Me-CMC: 3.2, 4.2, and 5.2%; 250 kDa: 1.2, 2.2, and 3.2%). Passage 2 NP cells were resuspended in a small volume of 0.05% photoinitiator and then homogeneously mixed with dissolved Me-CMC at $30 \times 10^6$ cells/mL. The seeding density was selected based on previous studies using cell-seeded constructs for engineering of cartilaginous tissues. Solutions were cast at final concentrations of 3, 4, and 5% (90 kDa Me-CMC) and 1, 2, and 3% (250 kDa Me-CMC) in a custom-made glass casting device. The mixtures were exposed to longwave UV light (EIKO, Shawnee, Kans., peak 368 nm, 1.2 W) for 10 minutes to produce covalently crosslinked hydrogel disks of 8-mm diameter×2-mm thickness. Each hydrogel was incubated in 3 mL of growth medium (DMEM with 10% FBS, 100 U/mL penicillin, 100 μg/mL streptomycin, and 0.075% sodium bicarbonate) at 37° C., 5% CO2. At day 1, the medium was fully exchanged with vitamin C (L-ascorbic acid) supplemented medium (growth medium with 50 μg/mL L-ascorbic acid), which was used for the remainder of the study and replaced every 2-3 days. Initial viability studies (described below) were performed using gels cast at 5-mm diameter×2-mm thickness and were incubated in 1.5 mL growth medium.

Cell Viability and Dynamic Mechanical Testing

Constructs were evaluated for viability using the MTT Assay Kit (ATCC). Preliminary screening studies examined the effects of weight percent and molecular weight on cell viability and the elastic mechanical properties of 3, 4, and 5% 90 kDa Me-CMC and 1, 2, and 3% 250 kDa Me-CMC. Cell viability was assessed at days 1 and 7 using the MTT (3-(4, 5-dimethylthiazolyl-2)-2,5-diphenyltetrazolium bromide) proliferation assay kit (ATCC, Manassas, Va.). Photocrosslinked Me-CMC hydrogels (n=4) were incubated in 1 mL of growth medium supplemented with 100 μL of yellow tetrazolium MTT for 4 hours at 37° C., 5% CO2, shielded from light. Hydrogels were then homogenized and formazan crystals were extracted using the MTT detergent solution (MTT cell proliferation assay kit, ATCC) for an additional 4 hours at room temperature, shielded from light. Total absorbance of the solubilized product was quantified at 570 nm using a Bio-Tek Synergy-HT microplate reader (Winooski, Va.). MTT absorbance values were compared between samples and to cell-free control gels to quantify relative viability. Day 7 measurements were also normalized to day 1 values to determine loss of viability over time.

Cell viability of 2% 250 kDa CMC constructs was qualitatively assessed at day 0 (one hour after casting), day 1, and day 7 using the Live/Dead kit (Invitrogen). Samples were rinsed in DPBS and then incubated in Live/Dead solution (1 mM calcein AM, 1 mM ethidium homodimer-2) for 45 minutes. Images were captured using a Zeiss Axiovert 200 microscope.

At day 7, a Dynamic Mechanical Analyzer (DMA) 8000 (PerkinElmer, Inc., Waltham, Mass.) testing apparatus was used to determine the elastic modulus of Me-CMC hydrogels at the weight percents described above. Samples (n=5) were rinsed in DPBS and loaded into the DMA. Unconfined compression testing was performed at 25° C. at a strain rate of 10%/minute. The modulus was determined from the linear region of the stress versus strain curves at strains between 5% and 20%.

Swelling Ratio

Following the initial studies examining cell viability and elastic mechanical properties, 4% 90 kDa, 2% 250 kDa, and 3% 250 kDa Me-CMC hydrogels were chosen for further characterization. The equilibrium weight swelling ratio, $Q_w$, was determined for these formulations at days 1, 7, and 14 for cell-laden and cell-free control samples (n=4). Constructs were weighed to determine the wet weight ($W_s$), lyophilized, and then weighed again to determine dry weight ($W_d$). $Q_w$ was calculated using the following equation:

$$Q_w = W_s/W_d$$

Characterization of Equilibrium Mechanical Properties

Based on the early screening studies, unconfined compression testing was conducted on 4% 90 kDa, 2% 250 kDa, and 3% 250 kDa Me-CMC cell-laden and cell-free control samples (n=5) at days 1, 7, and 14 to measure the equilibrium Young's modulus ($E_y$). The mechanical testing device is based on a similar setup described by Soltz and Ateshian. The device consists of a computer-controlled stepper motor (Oriel Corp., Model 18515, Stratford, Conn.) that prescribed a displacement on the specimen using a steel indenter with glass platen attachment. A data card and Lab VIEW software (National Instruments, Austin, Tex.) were used for controlling the stepper motor and data acquisition. Displacement was measured using a linear variable differential transformer (Schaevitz, Model PR812, Hampton, Va.), and the load applied was measured using a 250 g load cell (Sensotec, Model 31, Columbus, Ohio). Samples were compressed between two impermeable glass platens in a DPBS bath. The unconfined compression testing protocol was comprised of a creep test followed by a multi-ramp stress-relaxation test. The creep test consisted of a 1 g tare load at 10 μm/s ramp velocity for 1800 seconds until equilibrium was reached (equilibrium criteria: <10 μm change in 10 minutes). The multi-ramp stress-relaxation test consisted of three 5% strain ramps, each followed by a 2000 second relaxation period (equilibrium criteria: <0.5 g change in 10 minutes). Equilibrium stress was calculated at each ramp using surface area measurements and plotted against the applied strain. An average equilibrium Young's modulus was calculated from the stress versus strain curves and reported for each sample.

Histology and Immunohistochemistry

GAG deposition was visualized by staining 8 μm sections with a 1% solution of Safranin-O (Sigma). Cell-laden hydrogels were fixed for 45 minutes in acid formalin at room temperature and processed for paraffin embedding after graded serial ethanol dehydration. Samples were sectioned at a thickness of 8 μm, and hematoxylin and eosin staining was conducted to visualize cellular distribution throughout the hydrogel. Immunohistochemical analyses were performed to assess extracellular matrix accumulation of chondroitin sulfate proteoglycan (CSPG). Samples were treated with 0.5N acetic acid for two hours at 4° C. Non-specific binding was blocked using 10% goat serum (Invitrogen) in DPBS. A monoclonal antibody to CSPG (1:100 dilution in blocking solution) (Sigma) was used, followed by incubation in biotinylated goat/anti-mouse IgM secondary antibody (1:50 dilution in blocking solution) (Vector Labs, Burlingame, Calif.). A peroxidase-based detection system (Vectastain Elite ABC, Vector Labs) and 3,3' diaminobenzidine (Vector Labs) as the chromagen were used according to the manufacturer's protocols to detect ECM localization. Non-immune controls were processed in blocking solution without primary antibody. Samples were viewed with a Zeiss Axioskop 40 optical microscope and images were captured using AxioVision software.

Collagen ELISA

COL II was quantified using an indirect ELISA with a monoclonal antibody (DSHB) and normalized to DNA measured using the PicoGreen DNA assay (Invitrogen)

Image Analysis

Disk diameter was measured using Scion Image (Scion Corporation).

Statistical Analysis

A t-test was performed to determine the effect of weight percent on disk diameter and the effect of time on normalized COL II production. Significance was set at $p<0.05$. Data represent the mean±s.d. (n=4).

A one-way analysis of variance (ANOVA) was performed on compressive modulus data to determine the effect of weight percentage. A two way ANOVA was conducted to determine the effect of time and weight percentage on the swelling ratio and mitochondrial activity as a measure of cell viability. A three-way ANOVA was conducted on swelling and $E_y$ data for 4% 90 kDa, 2% 250 kDa, and 3% 250 kDa Me-CMC constructs to determine the effects of time, cells, and starting material. A two-way ANOVA was performed on equilibrium Young's modulus measurements for 3% 250 kDa Me-CMC constructs to examine the effects of time and cells. A Tukey post-hoc test was performed to detect significant differences between groups. All results are presented as mean±standard deviation with statistical significance defined as p<0.05. Statistical analyses were completed using JMP statistical software (SAS Institute, Cary, N.C.).

Example 2

Methylcellulose Hydrogels are Effective as Soft Tissue Filler in situ

Macromer Synthesis

Methacrylated methylcellulose (MA-MC) was synthesized through esterification of hydroxyl groups based on previously described protocols (FIG. 4). Briefly, 1 gram of 15 kDa MC (Sigma, St. Louis, Mo.) was dissolved in 35 mL of sterile water at a temperature of 80° C. To this solution, 65 mL of sterile water at 4° C. was added and stirred f or 30 minutes yielding a 1 wt % MC solution. A 5% theoretically modified solution of MC was prepared by reacting methacrylic anhydride (Sigma, St. Louis, Mo.) in 20-fold excess to the 1 wt % MC over 24 hours at 4° C. with periodic adjustments to pH 8.0 using 3N NaOH (approximately 12 times over the course of the reaction). The modified MC solution was purified via dialysis for at least 48 hours against sterile water (Spectra/Por 1, MW 5-8 kDa, Rancho Dominguez, Calif.) to remove excess methacrylic anhydride and the final product was recovered by lyophilization. Methacrylation was confirmed using $^1$H-NMR. Purified MA-MC was recovered by lyophilization and stored at −20° C.

NMR Analysis

1H-NMR (360 MHz, DMX360, Bruker, Madison, Wis.) was performed on acid hydrolyzed MA-MC to confirm the degree of substitution of purified MA-MC. Briefly, a 20-mg sample of lyophilized MA-MC was dissolved in 20 mL of sterile water and underwent acid hydrolysis at a pH of 2.0 at 80° C. for 2 hours. The pH of the hydrolyzed solution was re-adjusted to 7.0, recovered via lyophilization and resuspended in $D_2O$. Molar percent of methacrylation was determined by the relative integrations of the methacrylate proton peaks (methylene, δ=6.0 ppm and 5.6 ppm and the methyl peak, δ=1.8 ppm) to carbohydrate protons.

Photocrosslinked Methylcellulose Hydrogel Formation

The MA-MC lyophilized product was dissolved in 0.05 wt % photoinitiator, 2-methyl-1-[4-(hydroxyethoxy)phenyl]-2-methyl-1-propanone (IRGACURE® 2959, 12959, Ciba Specialty Chemicals, Basel, Switzerland) at 2 wt %, 4 wt % and 6 wt % in Dulbecco's Phosphate Buffered Saline (DPBS) at 4° C. Homogeneous solutions were poured into custom-made glass casting devices with a polysulfone insert and exposed to UV light (EIKO, Shawnee, Kans., peak 368 nm, 1.2 W) for 10 minutes. Photocrosslinked hydrogels, 2-mm in thickness and 8-mm in diameter, were used for all examples.

Swelling Ratio

The equilibrium weight swelling ratio, Qw, was determined for 2 wt %, 4 wt % and 6 wt % MA-MC hydrogels. Cast hydrogels were placed in 24-well plates containing 1 mL of DPBS per well. At 0.5, 1, 4, 16 and 24 hours, hydrogels were removed from DPBS and placed in pre-weighed 1.5 mL microcentrifuge tubes. The wet weight, QS, was obtained prior to freezing at −80° C. Frozen samples were then lyophilized and re-weighed to determine the dry weight, Qd. The swelling ratio was calculated using the following formula:

$$Q_W = Q_S / Q_D$$

Mechanical Testing

A Dynamic Mechanical Analyzer (DMA) 8000 (PerkinElmer, Inc, Waltham, Mass.) testing apparatus was used to determine the compressive modulus of MA-MC hydrogels at various weight percentages. Hydrogels at 2 wt %, 4 wt %, 5 wt % and 6 wt % were allowed to equilibrate overnight in DBPS at 37° C. Samples for mechanical testing (n=5 per weight percentage) were loaded into the DMA and submerged in 2 mL of DPBS. Unconfined compression testing was performed at 25° C. The modulus was determined from the linear region of the stress verses strain curves at strains less than 20%.

Cytotoxicity

The effect of MA-MC hydrogels on cell viability was assessed by coculturing human dermal fibroblasts (hDFs) in the presence of MA-MC gels. Second passage hDFs were plated at 20,000 cells per well on tissue culturetreated polystyrene 12-well plates in Dulbecco's Modified Eagle Medium supplemented with 10% fetal bovine serum (Hyclone, Logan, Utah), 0.075% sodium bicarbonate, 100 U/mL penicillin and 100 μg/mL streptomycin. On day 1, transwell inserts were placed in each well along with 2 wt % and 6 wt % MA-MC hydrogels (n=4-5 hydrogels per weight percentage). An additional 2 mL of media was added to each well to cover the hydrogels. Medium was changed every third day. Cell monolayers without MA-MC hydrogels served as cell-only controls. On days 3 and 5, the transwell inserts and hydrogels were removed. The medium was aspirated and replaced with 1 ml of fresh media. A 100 μL, volume of WST1 reagent (Roche Applied Science, Indianapolis, Ind.) was added to each well to measure cell viability. The tetrazolium salt, WST-1, is cleaved by mitochondrial dehydrogenases in viable cells to form the water soluble product formazan. After 4 hours at 37° C., the formaza n dye was quantified at 570 nm on the Bio-Tek Synergy-HT microplate reader (Winooski, Vt.).

In Vivo Degradation and Biocompatibility

A subcutaneous pouch mouse model was used to evaluate the biocompatibility of MA-MC gels in a non-immunocompromised host. A longitudinal skin incision was made on the dorsa of female, 4-week old CD-1 mice (Charles River Laboratories, Wilmington, Mass.) under an approved University of Pennsylvania animal protocol (#800209). Four separate subcutaneous pockets were created by blunt dissection close to each limb and four MA-MC hydrogels of the same weight percentage (2 wt % or 6 wt %) were implanted per mouse. At 7, 30 and 80 days, the mice were euthanized and the gels excised for histological processing. Gels within their fibrous capsules were fixed in 4% paraformaldehyde for 20 minutes. Samples were dehydrated in a graded series of ethanol prior to paraffin embedding and sectioned using a Lieca microtome (Model 2030, Nussloch, Germany). Hematoxylin and eosin staining was performed to visualize fibrous capsule thickness and cellularity.

Figure 5:
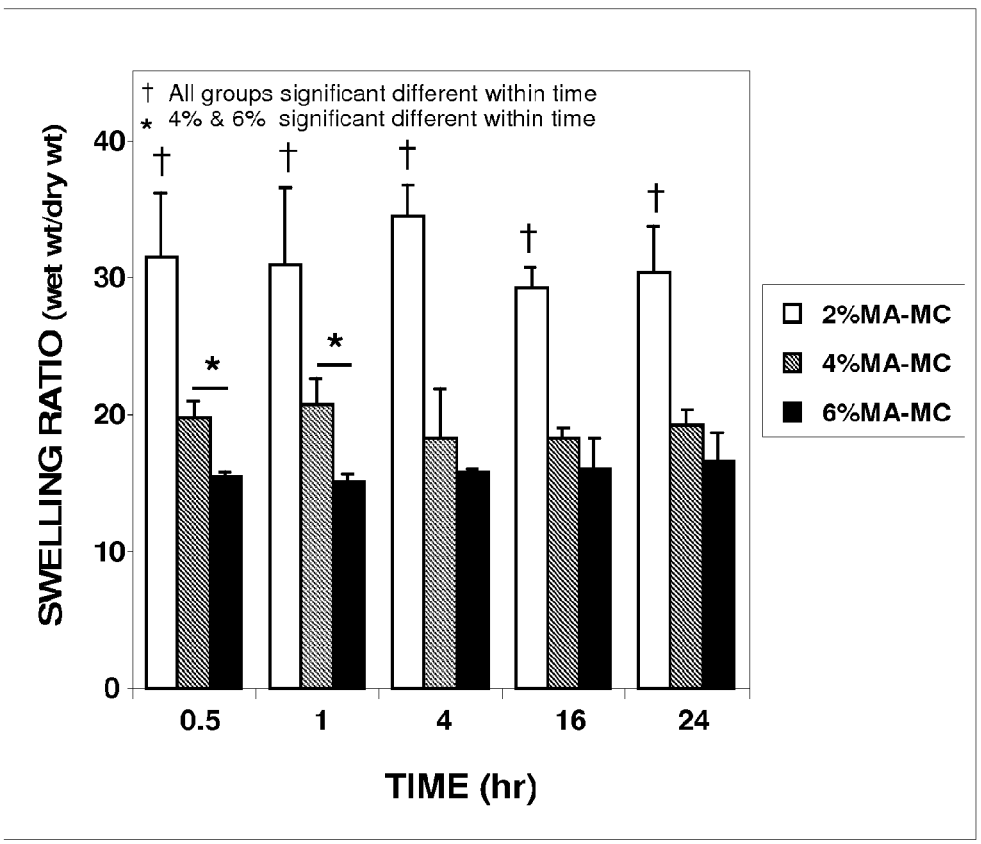
FIG. 5 shows swelling ratios of 2 wt %, 4 wt % and 6 wt % MA-MC hydrogels over 24-hours (n=3 hydrogels per weight percentage). Statistical significance is defined as p<0.05. Dagger, denotes statistical difference between all weight percentages. Asterisks, denotes statistical difference between 4 wt % and 6 wt % MA-MC hydrogels.

Methylcellulose was successfully modified at 2.3% methacrylation as verified by 1H-NMR. At 2 wt %, 4 wt %, 5 wt %, and 6 wt %, MA-MC dissolved in 0.05 wt % and exposed to UV light formed stable hydrogels. The swelling ratios of 2 wt %, 4 wt % and 6 wt % MA-MC hydrogels were constant over 24 hours as depicted in FIG. 5. There was a minimal change in hydrogel diameter in comparison to as-cast hydrogel controls. At each time point, the swelling ratio of 2 wt % MA-MC hydrogels was significantly greater than both 4 wt % and 6 wt % MA-MC hydrogels (p<0.001). The swelling ratio of 4 wt % hydrogels was greater than that of 6 wt % MA-MC hydrogels at 0.5-hour and 1-hour (p<0.05).

Figure 6:
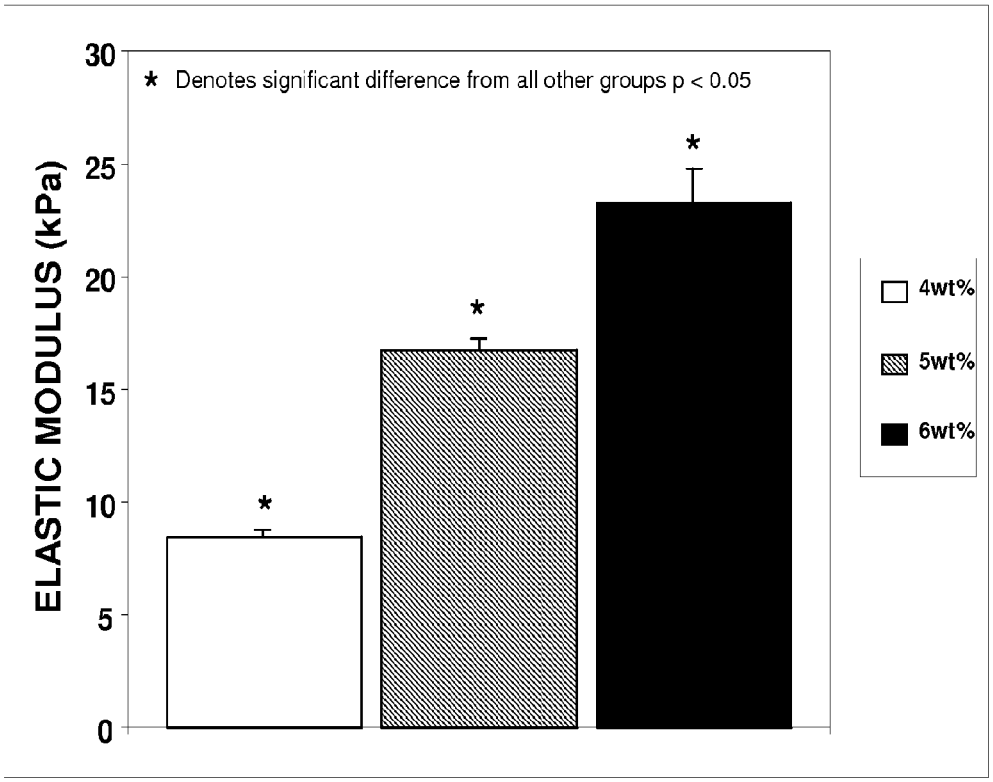
FIG. 6 shows compressive modulus of 4 wt %, 5 wt % and 6 wt % MA-MC hydrogels 24-hours after casting (n=5-7 hydrogels per weight percentage). There was significant variation in modulus across all groups (p<0.05)

Compression testing was performed on 4 wt %, 5 wt % and 6 wt % MA-MC hydrogels. Despite stable hydrogel formation, 2 wt % MA-MC samples were too weak to test mechanically. The 6 wt % MA-MC hydrogels had the largest compressive modulus of 23.21±1.55 kPa and the compressive modulus for each group (4 wt %, 5 wt % and 6 wt %) was significantly different from one another (p<0.05) (FIG. 6).

Figure 7:
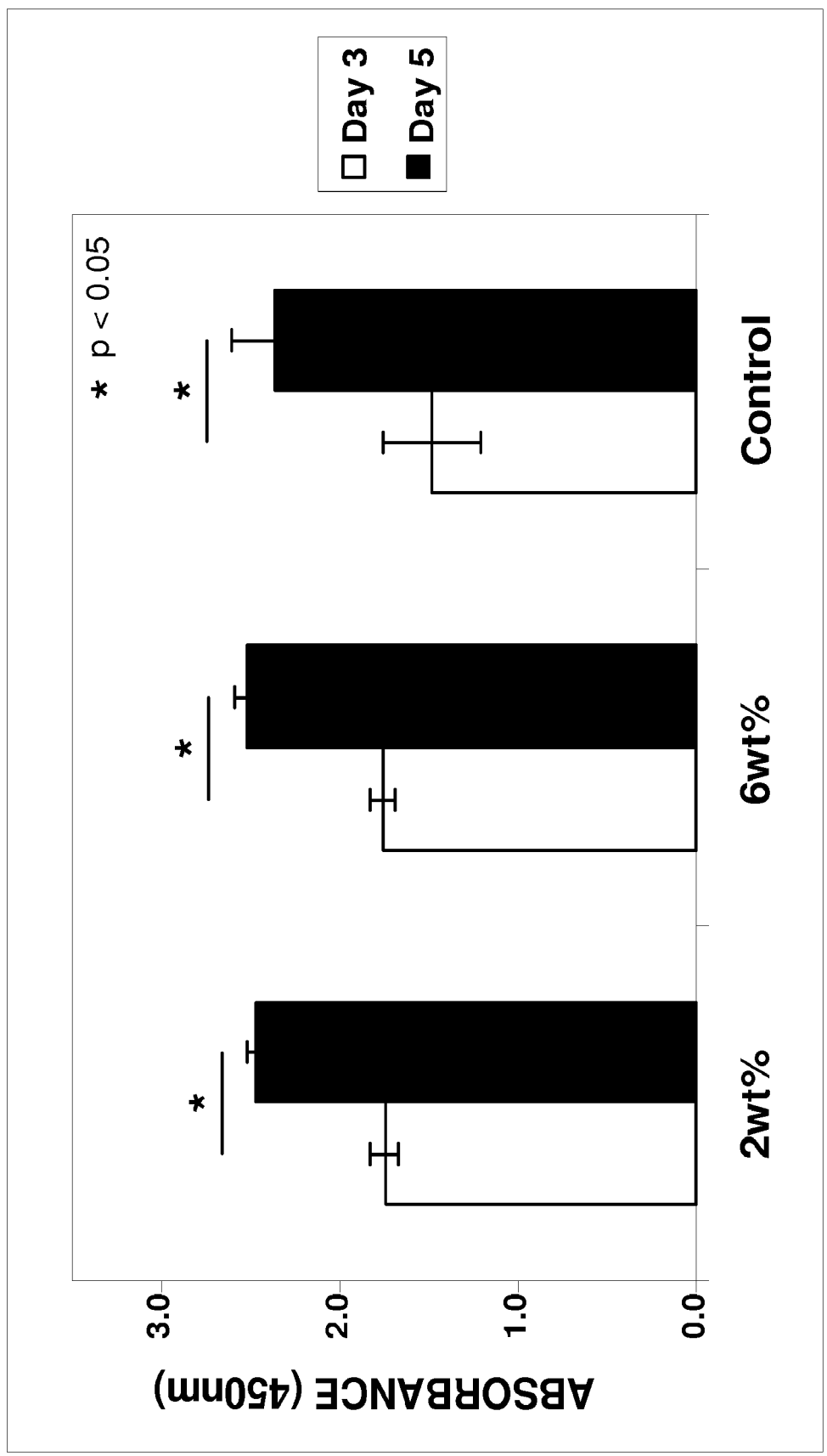
FIG. 7 shows cytotoxicity assessment of 2 wt % and 6 wt % MA-MC hydrogels cocultured in the presence of human dermal fibroblasts (hDF) grown in monolayer (n=4-5 hydrogels per weight percentage)

When co-cultured with hDFs in monolayer, 2 wt % and 6 wt % MA-MC hydrogels did not exhibit cytotoxic effects. At days 3 and 5, both formulations allowed for normal cell growth and proliferation similar to hydrogel-free controls (FIG. 7). Human dermal fibroblast viability was significantly greater at day of co-culture in comparison to day 3 (p<0.05) for all groups.

In vivo biocompatibility studies were conducted on the highest and lowest weight percent formulations of MC that produced stable gels. Normal CD-1 mice maintained normal feeding and activity levels with no superficial skin lesions at 7, 30 and 80 days after subcutaneous implantation of 2 wt % and 6 wt % MA-MC hydrogels. Gross observation of hydrogels at Day 7 suggested a minimal inflammatory response with the absence of pus, redness and thin fibrous capsule formation. As seen in FIG. 8, 2 wt % MA-MC hydrogel appeared intact in vivo, however, once excised these hydrogels were difficult to handle and did not retain their shape. Conversely, gross observations revealed that 6 wt % MA-MC hydrogels maintained their dimensions and structural integrity both in vivo, and once excised, ex vivo. These observations were similar at 7 and 30 days. At 80 days, only fragments of 2 wt % MA-MC hydrogels were present in vivo, while at the higher weight percentage, MA-MC hydrogels remained intact (FIG. 9). Excised 80 day 6 wt % MA-MC hydrogels were tested mechanically and the compressive modulus after 80 days in vivo (26.82±5.25 kPa) was not significantly different from the modulus prior to implantation (23.21±1.55 kPa). The fibrous capsule that encapsulated 6 wt % MA-MC hydrogels at 30 and 80 days was visualized by H&E staining (FIG. 10). At both time points, the fibrous capsule circumscribed the hydrogel with no cell infiltration. The capsule thickness did not change over time, measuring approximately 50 nm in width.

Example 3

Figure 13:
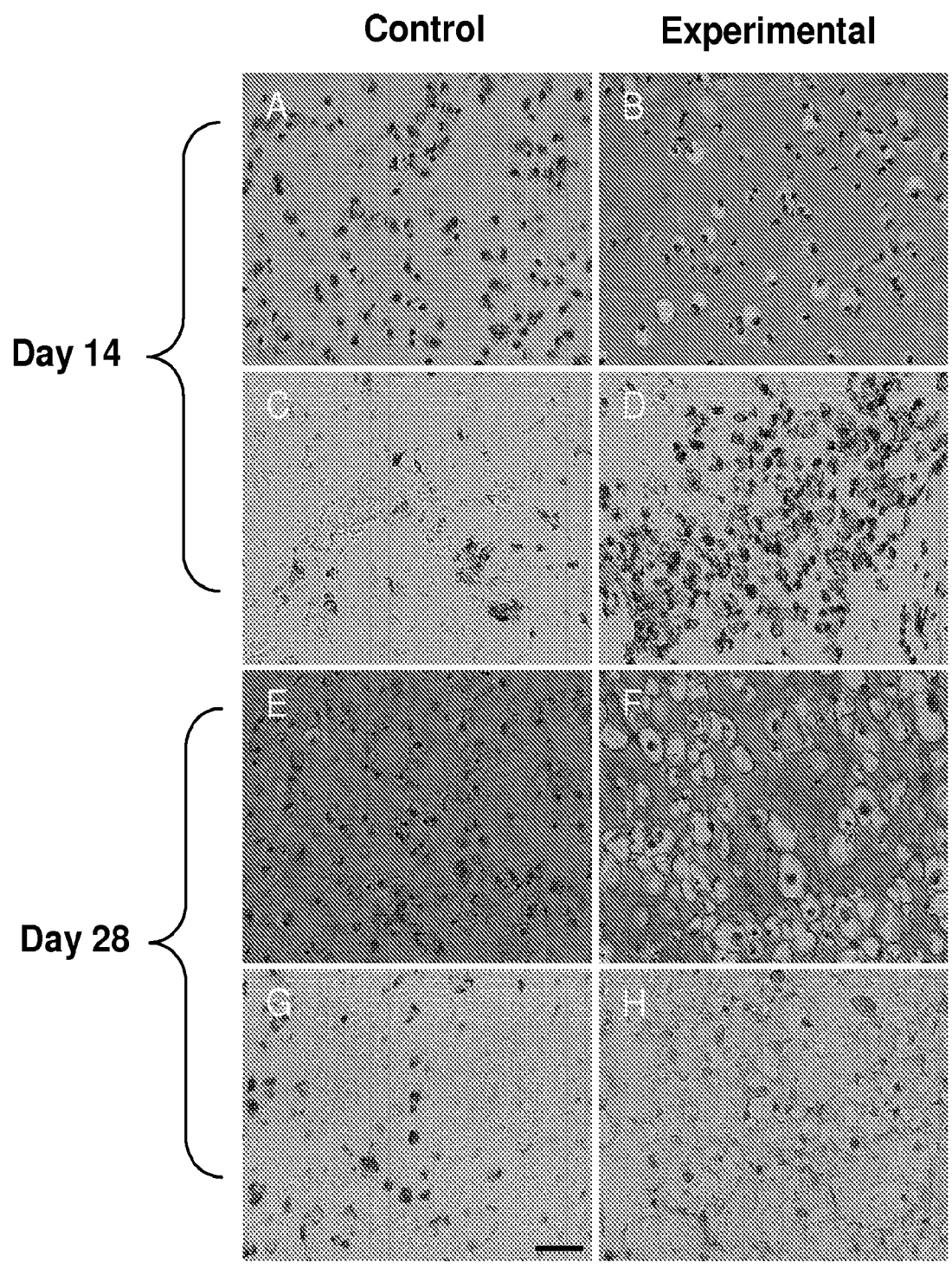
FIG. 13 shows human dermal fibroblast-laden 2% CMC hydrogels at day 14 (A-D) and 28 (E-H). (A,B,E,F) H&E histology, and (C,D,G,H) CSPG immunolocalization. Bar=50 µm for all panels.

Chondroinduction of Human Dermal Fibroblasts in Photocrosslinked Carboxymethylcellulose Hydrogels In this Example, postnatal human dermal fibroblasts (passage 5) were photoencapsulated in 2% CMC hydrogels (60× $10^6$ cells/mL) as described above for NP cells. For chondroinduction, cell-laden hydrogels were cultured in MEM supplemented with 10% FBS, lactic acid (40 mM), staurosporine (200 nM) and antibiotics. After an initial 24-hour treatment period, all experimental cultures were rinsed with PBS and maintained in serum-free, chemically-defined medium consisting of MEM with 1% insulin-transferrin-selenium, 4.5 g/L glucose, 50 µg/ml ascorbic acid and antibiotics. These culture conditions have been shown to promote chondrogenesis in human dermal fibroblasts. Additional fibroblast control hydrogels were cultured in serum-containing medium for 24 hours (MEM supplemented with 10% FBS and antibiotics) and maintained in serum-free, chemically-defined medium for the duration of the study (as with experimental cultures). At 14 and 28 days, the constructs were characterized for cellular organization (H&E staining) and CSPG elaboration (FIG. 13). After 14 days, fibroblast-laden hydrogels cultured in chondroinductive media exhibited rounded cells in lacuna-like cavities (FIG. 13B) with extensive pericellular CSPG staining (FIG. 13D). In contrast, control cultures displayed a less spherical cell morphology (FIG. 13A) and minimal CSPG elaboration (FIG. 13C). By 28 days, experimental cultures resembled native cartilage with cells localized in lacunae (FIG. 13F) and CSPG distributed more evenly throughout the hydrogels (FIG. 13H). Taken together, these findings suggest that human dermal fibroblasts encapsulated in polysaccharide hydrogels and maintained in chondroinductive medium are capable of forming constructs that possess histological features consistent with cartilaginous tissues.

Example 4

Modification of CMC with Methacrylate Group to Produce Photo-Crosslinked Hydrogels In this Example, 90 kDa and 250 kDa CMC polymers were modified with functional methacrylate groups and photo-crosslinked to produce hydrogels at different macromer concentrations. At 7 days, bovine nucleus pulposus (NP) cells encapsulated in these hydrogels were viable, with values for the elastic modulus ranging from 1.07±0.06 to 4.29±1.25 kPa. Three specific formulations were chosen for further study based on cell viability and mechanical integrity assessments: 4% 90 kDa, 2% 250 kDa, and 3% 250 kDa CMC. The equilibrium weight swelling ratio of these formulations remained steady throughout the two-week study (46.45±3.14, 48.55±2.91, and 42.41±3.06, respectively). The equilibrium Young's modulus of all cell-laden and cell-free control samples decreased over time, with the exception of cell-laden 3% 250 kDa CMC constructs, indicating an interplay between limited hydrolysis of interchain crosslinks and the elaboration of a functional matrix. Histological analyses of 3% 250 kDa CMC hydrogels confirmed the presence of rounded cells in lacunae and the pericellular deposition of chondroitin sulfate proteoglycan, a phenotypic NP marker. Taken together, these studies show the use of photo-crosslinked CMC hydrogels as tunable biomaterials for NP cell encapsulation.

CMC was successfully modified (90 kDa CMC: 3.29% methacrylation; 250 kDa CMC: 2.87% methacrylation), as verified by 1H-NMR. Initial studies examined the effects of weight percent and molecular weight on cell viability and elastic mechanical properties. Weight percent ranges were selected based on ease of handling (a function of pre-crosslinked polymer solution viscosity) and stable hydrogel formation.

Figure 15A:
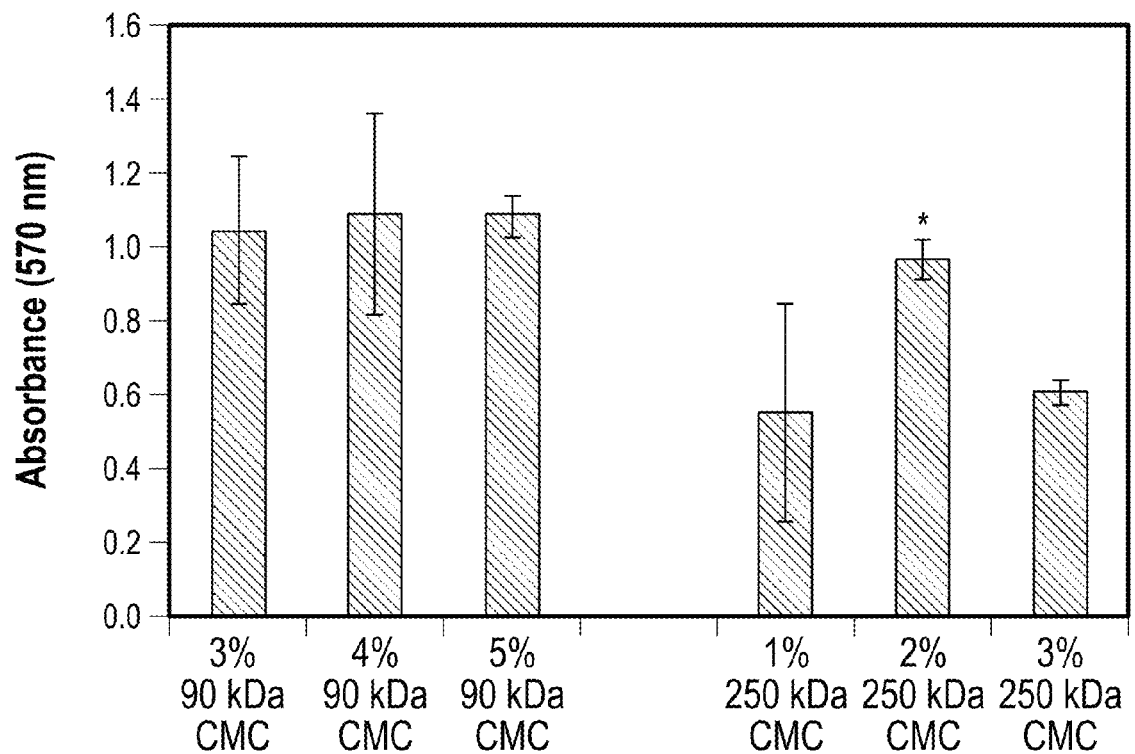
FIG. 15 shows mitochondrial activity measurements (MTT) at day 7 for (A) photocrosslinked 90 kDa and 250 kDa CMC hydrogels (n=4) at various weight percents encapsulated with bovine nucleus pulposus cells at $30 \times 10^6$ cells/mL. (B) Day 7 MTT results normalized to respective day 1 measurements. Representative day 7 MTT stereomicrograph images of 3% 90 kDa (C), 4% 90 kDa (D), 5% 90 kDa (E), 1% 250 kDa (F), 2% 250 kDa (G), and 3% 250 kDa (H) CMC cell-laden hydrogels (scale in mm) Live/Dead images of 2% 250 kDa CMC samples at days 0 (I), 1 (J), and 7 (K) with live cells stained green and dead cells shown in red (bar=100 lJ,m). Significance set at p<0.05. * Significant effect of weight percent. + Significant vs. day 1.
Figure 15B:
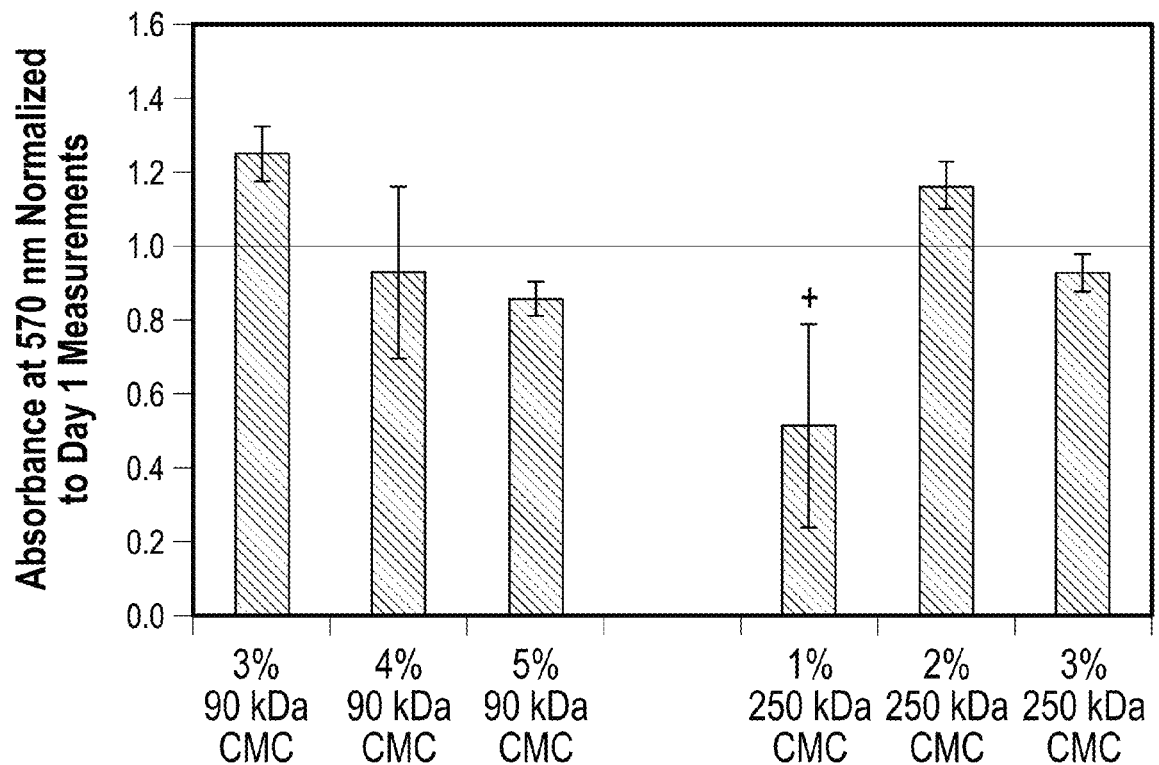

The formulations selected for initial analysis were 3, 4, and 5% 90 kDa CMC and 1, 2, and 3% 250 kDa CMC. Bovine NP cells were encapsulated in these gel formulations and samples were isolated at days 1 and 7 to assess cell viability using the MTT assay. Overall, evenly distributed, viable cells were observed for all groups at both time points (FIG. 15 C-H). There were no significant differences in viability based on weight percent for 90 kDa CMC constructs at either time point (FIG. 15A). Day 1 viability in 3% 250 kDa CMC hydrogels was significantly lower than 1% 250 kDa CMC samples; however, this was not significant in comparison to 2% 250 kDa CMC constructs. By day 7, viability in 2% 250 kDa CMC samples was significantly higher than that for 1 and 3% counterparts (FIG. 15A). Day 7 normalized viability indicated no significant loss in viability over time for any group except 1% 250 kDa CMC constructs (FIG. 15B). Stable disks were formed for all groups at both molecular weights, with the exception of 1% 250 kDa CMC, which was not able to retain structural integrity (FIG. 15F).

Viability was also assessed qualitatively at days 0, 1, and 7 for 2% 250 kDa CMC constructs. A highly viable cell population (indicated in green) was observed on day 0 (one hour after casting) (FIG. 15I) and at day 1 (FIG. 15J), with some dead cells present (red). By day 7, the number of dead cells increased; however, the cell population remained largely viable (FIG. 15K).

Figure 1B:
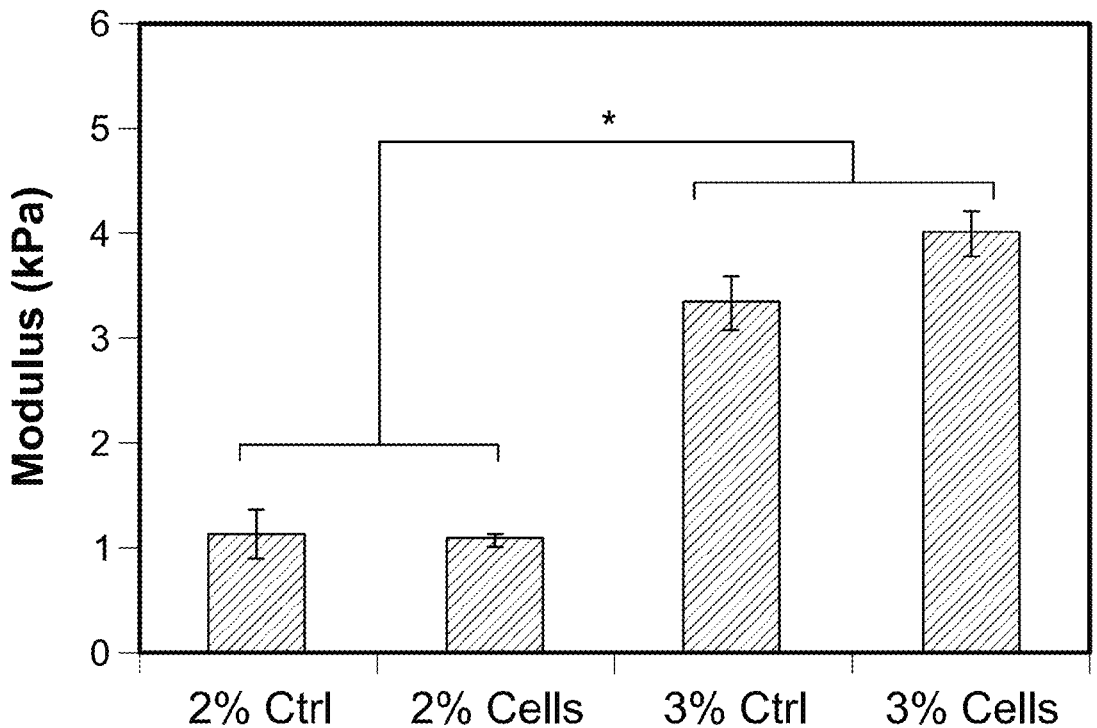

Elastic mechanical properties of cell-laden and cell-free control gels at these six formulations were also quantified at day 7. Although 3% 90 kDa CMC formed stable constructs, these samples were too weak to be mechanically tested and were excluded, as were the amorphous 1% 250 kDa CMC gels. Quantification of the elastic modulus determined no significant differences between cell-laden and cell-free hydrogels at day 7 in any group (FIG. 1). There was a significant overall effect of weight percent, as samples at higher concentrations exhibited a higher modulus (4% vs. 5% 90 kDa CMC and 2% vs. 3% 250 kDa CMC). From these preliminary studies, 4% 90 kDa CMC and 2% 250 kDa CMC were selected for further characterization.

Cell-laden and cell-free hydrogels composed of 4% 90 kDa CMC and 2% 250 kDa CMC were cast and analyzed at days 1, 7, and 14 to determine the swelling ratio and the equilibrium Young's modulus. Overall, there were no significant differences in swelling between cell-laden and cell-free hydrogels at either molecular weight at any time point ($Q_w$: 46.45±3.15 and 48.55±2.91 for 90 kDa and 250 kDa CMC, respectively). In addition, there was no significant effect of molecular weight (90 kDa vs. 250 kDa) at any time point, nor was there a significant effect of time, as $Q_w$ was stable over the 14-day study for all groups.

Figure 16:
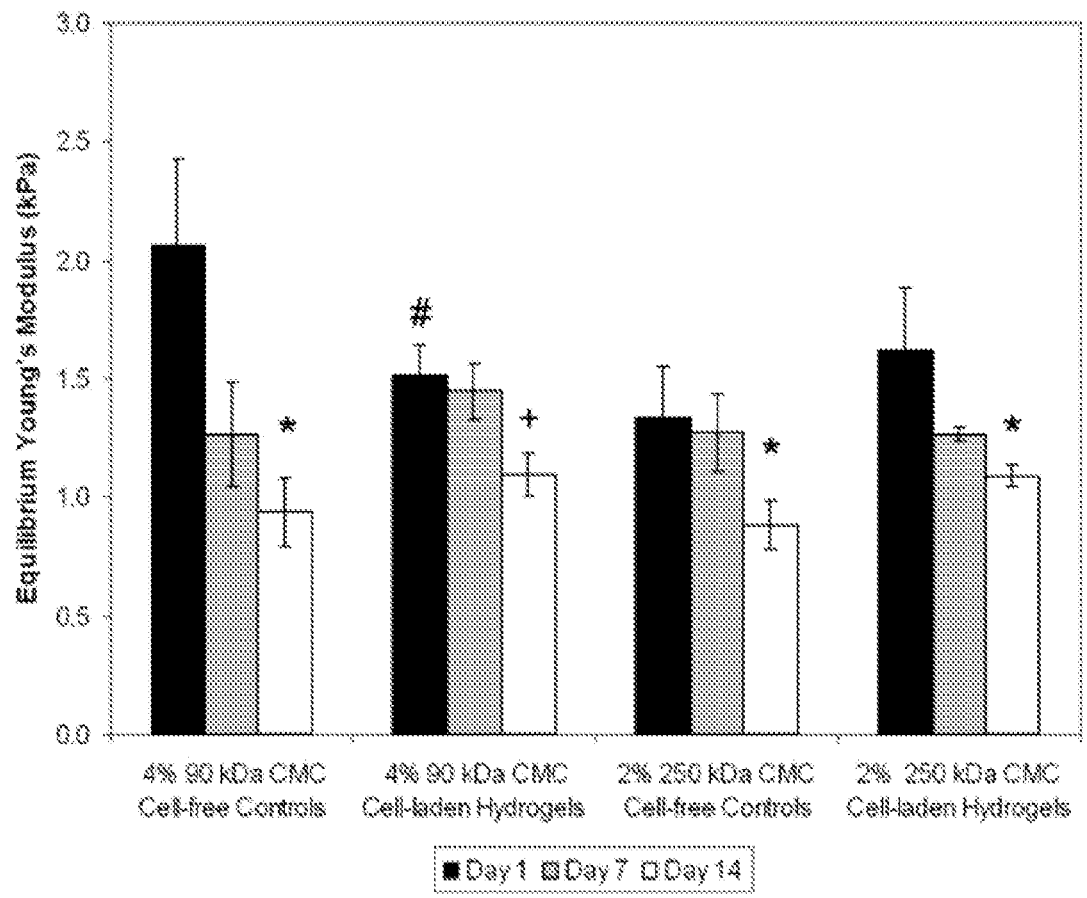
FIG. 16 shows Equilibrium Young's modulus for 4% 90 kDa and 2% 250 kDa CMC cell-free control and cell-laden hydrogels (n=5) over 14 days of in vitro culture. Significance set at p<0.05. *: Significant vs. day 1 within group. +: Significant vs. days 1 and 7 within group. #: Significant vs. corresponding cell-free control.

Unconfined compression testing of 4% 90 kDa CMC and 2% 250 kDa CMC constructs revealed a significant loss in mechanical properties over time for all groups (FIG. 16). Cell-laden and cell-free control hydrogels at both 4% 90 kDa CMC and 2% 250 kDa CMC exhibited a significant decrease in $E_y$ by day 14. Overall, there was no significant effect of CMC molecular weight (90 kDa vs. 250 kDa) nor of cells (cell-laden samples vs. cell-free controls) for any group, except 4% 90 kDa CMC at day 1.

Based on the steady decrease in mechanical properties observed for both 4% 90 kDa CMC and 2% 250 kDa CMC constructs, a higher weight percent gel was chosen to provide a stiffer initial environment. Cell-laden and cell-free 3% 250 kDa CMC hydrogels were cast and again analyzed at days 1, 7, and 14 to determine the swelling ratio, mechanical properties, and ECM accumulation. In contrast to 2% 250 kDa CMC constructs, the presence of cells in 3% 250 kDa CMC gels resulted in a significantly lower degree of swelling than was observed for cell-free controls ($Q_w$: 40.14±1.80 vs. 44.67±2.27, respectively). However, as for 2% 250 kDa CMC constructs, $Q_w$ for 3% 250 kDa CMC samples was stable over the 14-day study, with no effect of time observed for either cell-laden or cell-free control gels. Overall, $Q_w$ was significantly lower for 3% 250 kDa samples in comparison to both 4% 90 kDa and 2% 250 kDa CMC hydrogels (42.41±3.06 vs. 46.45±3.14 and 48.55±2.91, respectively).

Figure 12:
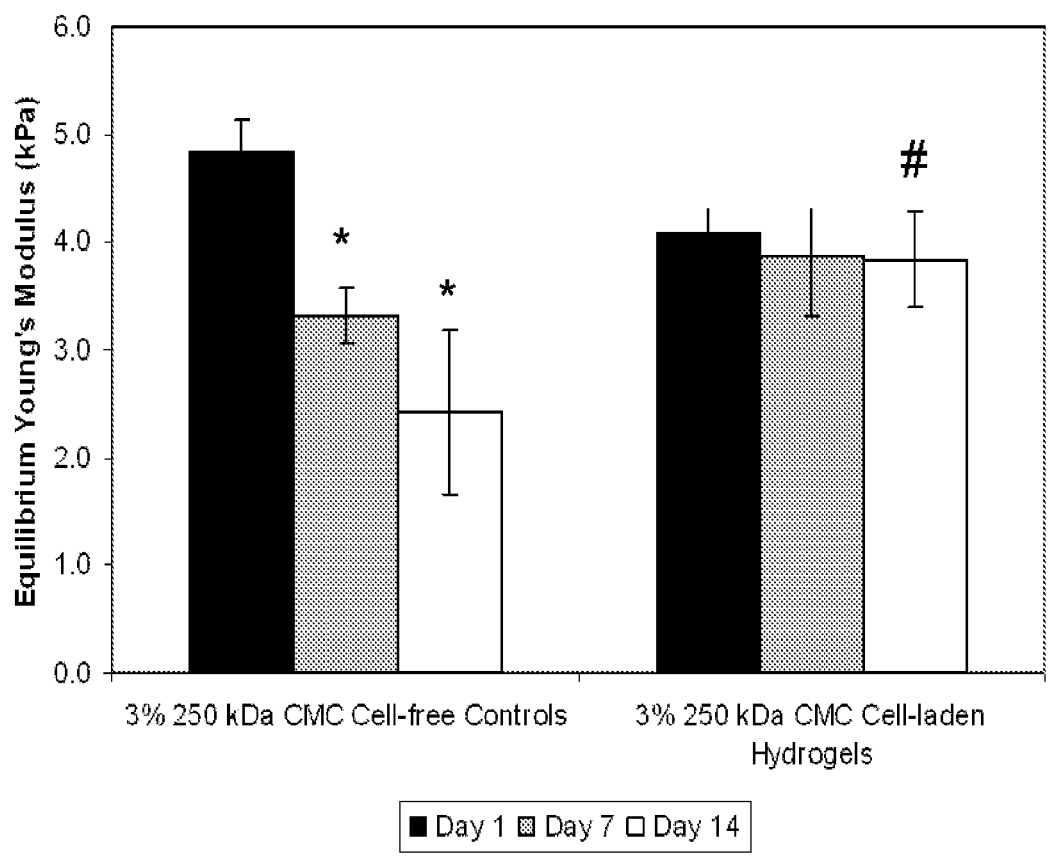
FIG. 12 shows equilibrium Young's modulus of CMC constructs over time. # indicates significant (p<0.05) effect of time within group. * indicates significant difference vs. cell-free control within time point. (n=4)

3% 250 kDa CMC samples were tested in unconfined compression to determine the equilibrium Young's modulus. A significant temporal decrease in mechanical properties was again observed for cell-free control gels (FIG. 12). In contrast, there was no significant effect of time observed for cell-laden constructs. By day 14, cell-free control gels were significantly weaker than their cell-laden counterparts. Overall, the average equilibrium Young's modulus for 3% 250 kDa CMC samples was significantly higher in comparison to both 4% 90 kDa and 2% 250 kDa CMC hydrogels (3.53±0.87 kPa vs. 1.37±0.44 kPa and 1.27±0.35 kPa, respectively).

Figure 11:
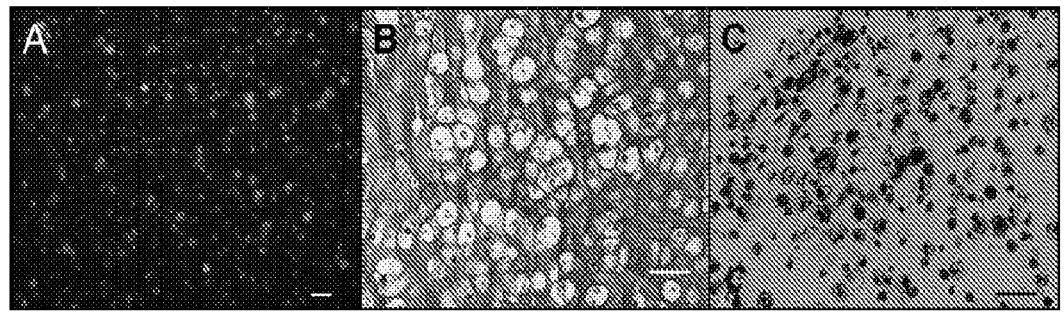
FIG. 11 shows NP cell-laden 3% CMC hydrogels at day 14. (A) Live/Dead fluorescence micrograph (green=live, red=dead), (B) H&E histology, and (C) CSPG immunolocalization. Bar=50 µm.

Histological analyses conducted on 3% 250 kDa CMC constructs at day 14 confirmed a phenotypic rounded cellular morphology within the hydrogel, as determined by hematoxylin and eosin staining (FIG. 11A). By day 14, cells were localized in limited lacunae at the center of the construct and well-developed, extensive lacunae at the scaffold periphery. Immunohistochemical staining verified pericellular deposition of CSPG throughout the construct, with more pronounced interterritorial staining present at the periphery (FIG. 11B).

In this study, CMC was successfully modified with methacrylate groups to produce photocrosslinked hydrogels with tunable properties. In addition, this is the first investigation to demonstrate successful encapsulation of NP cells in photocrosslinked CMC hydrogels, showing that these materials can serve as alternate scaffolds for IVD replacement therapies.

Figure 14:
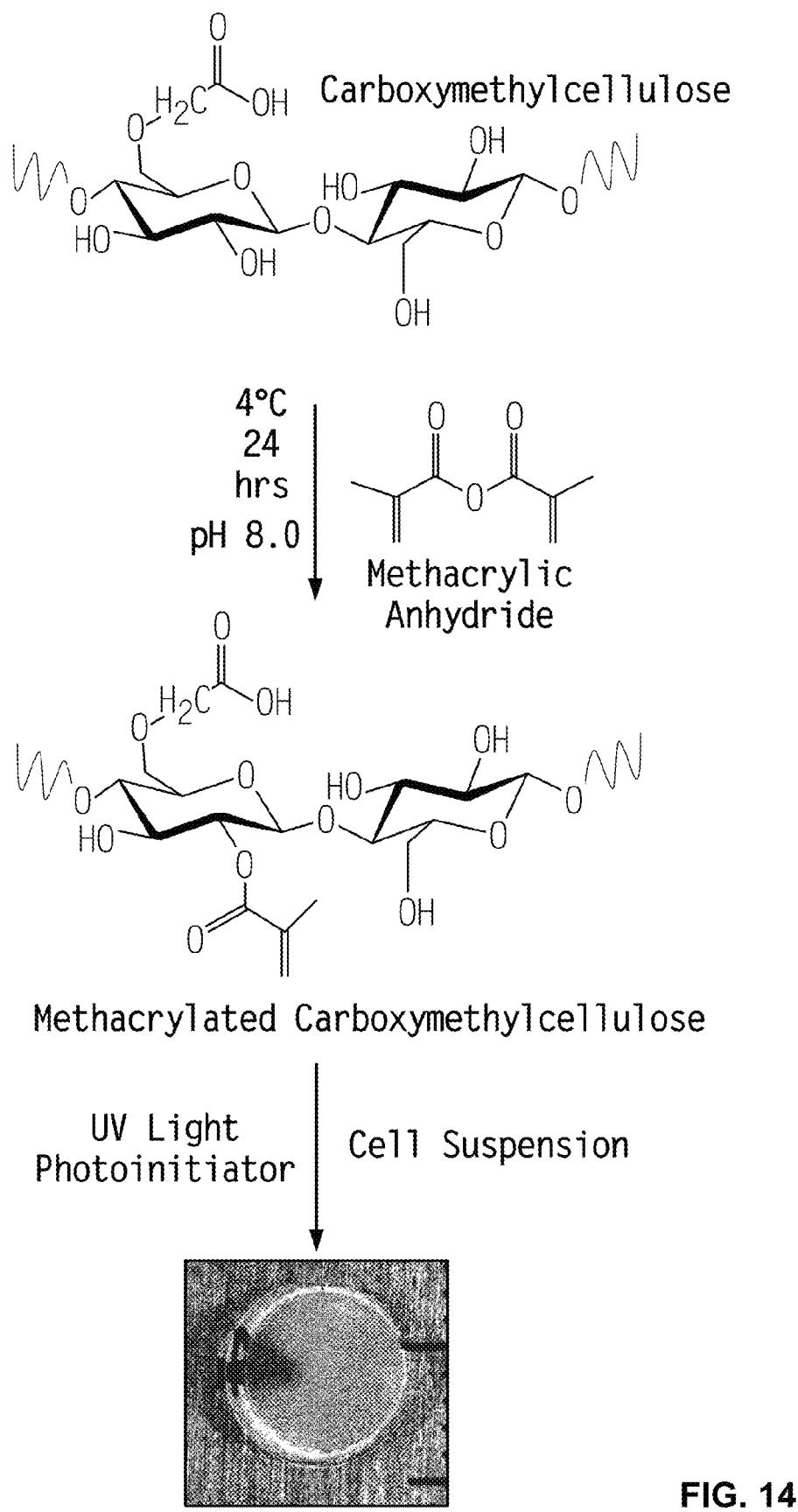
FIG. 14 illustrates the schematic of the synthesis of methacrylated carboxymethylcellulose.

Based on the results from our initial screening, the swelling ratio was characterized in cell culture medium for three formulations of CMC: 4% 90 kDa CMC and 2 and 3% 250 kDa CMC. $Q_w$ remained steady over time for all groups. Additional studies demonstrated similar results in physiological saline and simulated body fluid. A stable swelling ratio is important for potential IVD clinical applications as an intra-discal replacement material in order to prevent bulging and extrusion into the annulus fibrosus. Although $Q_w$ remained unchanged, the mechanical properties ($E_y$) of 4% 90 kDa CMC and 2% 250 kDa CMC constructs experienced a significant decrease over time for both cell-laden and cell-free constructs (FIG. 16). These two formulations were originally chosen for more extensive characterization. The equilibrium Young's modulus of these alginate constructs was ~1.25 kPa at day 1 and increased to ~4.31 kPa at 8 weeks, which indicated the elaboration of a functional matrix that closely approximates values of the native NP (~5 kPa). The results of our initial study showed that the elastic modulus for 4% 90 kDa CMC and 2% 250 kDa CMC constructs was ~1 kPa at day 7 (FIG. 1). As such, these formulations were selected for a more detailed analysis with the belief that the starting mechanical properties of the scaffold would allow for matrix accumulation, resulting in a temporal increase in modulus. However, $E_y$ exhibited a continual decrease over time for both groups. Because CMC is a derivative of cellulose, the polymer backbone is degraded by the plant-derived enzyme, cellulase. As this enzyme was not introduced into the system, the loss in mechanical properties was surprising. The decrease in modulus was observed for both cell-laden and cell-free constructs, indicating a non-cellular mediator of hydrogel weakening. Although the schematic in FIG. 14 shows methacrylation of the hydroxyl group off of the C2 carbon, theoretically, this could also occur at a hydroxyl bonded to the C6 carbon. This arm would be more susceptible to ester hydrolysis as the longer chain is less sterically hindered, thereby resulting in the cleavage of periodic interchain crosslinks without a significant loss in mass.

Due to the decrease in mechanical properties observed for 4% 90 kDa CMC and 2% 250 kDa CMC, a higher weight percent formulation was chosen to provide a higher crosslinking density. Although viability was robust in all concentrations of 90 kDa CMC (FIG. 15A), a higher weight percent at this molecular weight was not selected due to the large amount of starting material necessary and the increased concentration of lingering free radicals. Therefore, the 3% 250 kDa CMC formulation was selected. Similar to 4% 90 kDa and 2% 250 kDa hydrogels, 3% 250 kDa cell-free control samples also experienced a temporal decrease in mechanical properties (FIG. 12). However, the stiffer initial environment (~4 kPa) was on par with native NP tissue (~5 kPa) and cell-laden constructs elaborated a matrix that was able to overcome the decrease in mechanics and maintain the original modulus. Unlike the softer 4% 90 kDa and 2% 250 kDa CMC hydrogels, the partial hydrolysis of the stiffer 3% 250 kDa CMC constructs provided void space for the accumulation of secreted matrix macromolecules while maintaining sufficient structural integrity. Histological analyses showed cells localized in lacunae throughout the scaffold, as is typical of cartilaginous tissues (FIG. 11A), and the pericellular deposition of CSPG was observed with pronounced interterritorial staining at the periphery of the construct (FIG. 11B).

Although this study concentrated on characterizing the material properties (degree of swelling and modulus) of cell-free and cell-laden hydrogels, histological analyses confirmed the phenotypic rounded morphology and elaboration of characteristic proteoglycans (i.e., CSPG) by encapsulated NP cells at 14 days in vitro.

Taken together, these findings clearly show NP cell encapsulation by photocrosslinkable CMC hydrogels, as these biomaterials support NP cell viability and may be easily tailored for specific applications. Moreover, photocrosslinkable CMC may serve as a cost effective, biocompatible alternative to inert polymers, including PEO and PEG, and expensive bacterial- and animal-derived polysaccharides, such as hyaluronic acid and chondroitin sulfate, for use in the engineering of hydrated cartilaginous tissues.

Example 5

Media Formulation for NP Tissue Engineering by Comparing the Effects of Serum and TGF-$\beta_3$ on the In Vitro Culture of Cell-Laden CMC Constructs Materials and Methods
Macromer Synthesis Methacrylated carboxymethylcellulose (Me-CMC) was synthesized through esterification of hydroxyl groups based on previously described protocols (Burdick et al. 2005; Chou and Nicoll; Smeds et al. 2001). Briefly, a 20-fold excess of methacrylic anhydride (Sigma, St. Louis, Mo.) was reacted with a 1 wt % solution of 250 kDa CMC (Sigma) in RNAse/DNAse-free water over 24 hours at 4° C. The pH was periodically adjusted to 8.0 using 3N NaOH to modify hydroxyl groups of the polymer with functional methacrylate groups. The modified CMC solution was purified via dialysis for 96 hours against RNAse/DNAse-free water (Spectra/Por1, MW 5-8 kDa, Rancho Dominguez, Calif.) to remove excess, unreacted methacrylic anhydride. Purified Me-CMC was recovered by lyophilization and stored at −20° C. The degree of substitution was confirmed using $^1$H-NMR (360 MHz, DMX360, Bruker, Madison, Wis.) following acid hydrolysis of purified Me-CMC. Molar percent of methacrylation was determined by the relative integrations of methacrylate proton peaks (methylene, $\delta$=6.2 ppm and 5.8 ppm and the methyl peak, $\delta$=2.0 ppm) to carbohydrate protons.

Primary Cell Culture and Isolation

All cell culture supplies, including media, antibiotics, and buffering agents, were purchased from Invitrogen (Carlsbad, Calif.) unless otherwise noted. Discs C2-C4 were isolated from bovine caudal IVDs obtained from a local abattoir, and the NP was separated through gross visual inspection based on previous protocols (Chou et al. 2006; Chou et al. 2008). Tissue was maintained in Dulbecco's Modified Eagle Medium (DMEM) supplemented with 20% FBS (Hyclone, Logan, Utah), 0.075% sodium bicarbonate, 100 U/mL penicillin, 100 µg/mL streptomycin, and 0.25 µg/mL Fungizone reagent at 37° C., 5% $CO_2$ for two days prior to digestion to ensure no contamination occurred during harvesting. A single serum lot was used for all experiments to reduce potential variability in the cellular response.

Tissue was diced and NP cells were released by collagenase (Type IV, Sigma) digestion at an activity of 7000 U collagenase per gram of tissue. Following incubation in collagenase, undigested tissue was removed using a 40 µm mesh filter. Cells from multiple levels (C2-C4) were pooled and rinsed in sterile Dulbecco's Phosphate Buffered Saline (DPBS). These primary cells were plated onto tissue culture flasks and designated as passage 0. Cells were subcultured twice to obtain the necessary number of cells, and passage 2 cells were used in all experiments (Chou et al. 2006).

Cell Encapsulation in Photocrosslinked Hydrogels

Prior to dissolution, lyophilized Me-CMC was sterilized by a 30-minute exposure to germicidal UV light. The sterilized product was then dissolved to 2.75% in filter-sterilized 0.05 wt % photoinitiator, 2-methyl-1-[4-(hydroxyethoxy)phenyl]-2-methyl-1-propanone (IRGACURE® 2959, 12959, Ciba Specialty Chemicals, Basel, Switzerland), in sterile DPBS at 4° C. Passage 2 NP cells were resuspended in a small volume of 0.05% 12959 and then homogeneously mixed with dissolved Me-CMC at 30×10$^6$ cells/mL for a final concentration of 2.5%. The seeding density was selected based on previous studies using cell-seeded constructs for engineering of cartilaginous tissues (Chang et al. 2001; Hung et al. 2004; Iwasa et al. 2003; Mauck et al. 2002; Puelacher et al. 1994; Vunjak-Novakovic et al. 1998). The mixture was then exposed to long-wave UV light (EIKO, Shawnee, Kans., peak 368 nm, 1.2 W) for 10 minutes to produce covalently crosslinked hydrogel disks of 5-mm diameter×2-mm thickness. Each hydrogel was incubated in 1.5 mL of growth medium (DMEM with 10% FBS, 100 U/mL penicillin, 100 µg/mL streptomycin, and 0.075% sodium bicarbonate) at 37° C., 5% $CO_2$. At day 1, constructs were switched to the respective media formulations for the remainder of the study. DMEM medium was comprised of growth medium described above. CDM (chemically defined medium) was comprised of DMEM with 1% insulin-transferrin-selenium+universal culture supplement (BD Biosciences, San Jose, Calif.), 100 U/mL penicillin, 100 µg/mL streptomycin, 40 µg/mL L-proline (Sigma), 1 mM sodium pyruvate (Mediatech, Inc., Manassas, Va.), 50 µg/mL ascorbic acid 2-phosphate (Sigma), and 100 nM dexamethasone (Sigma) (Mackay et al. 1998). DMEM+ and CDM+constructs were further supplemented with 10 ng/mL rhTGF-$\beta_3$ (R&D Systems, Minneapolis, Minn.). This concentration was based on previous work in IVD and cartilage tissue engineering (Byers et al. 2008; Lima et al. 2007; Mackay et al. 1998; Miyanishi et al. 2006; Risbud et al. 2006).

Swelling Ratio

The equilibrium weight swelling ratio, $Q_w$, was determined at days 3, 14, and 28 (n=4). Constructs were weighed to determine the wet weight ($W_s$), lyophilized, and then weighed again to determine dry weight ($W_d$). $Q_w$ was calculated using the following equation:

$$Q_w = W_s/W_d$$

Biochemistry

Following lyophilization, total protein and DNA (n=4) were extracted at days 3, 14, and 28 by pepsin digestion based on previous studies (Chou et al. 2008). Briefly, lyophilized samples were pulverized and treated with pepsin in 0.05N acetic acid (1.9 mg/mL) for 48 hrs at 4° C. After this time, pepsin was neutralized by the addition of 10×TBS. Cell-free hydrogels (n=3) were maintained for all groups to serve as negative controls. Total DNA content was measured using the PicoGreen DNA assay (Singer et al. 1997) (Molecular Probes, Eugene, Oreg.) with calf thymus DNA as the standard. Briefly, 100 µL of PicoGreen dye was mixed with 100 µL of diluted sample or standard in a microplate which was then read at 480 nm excitation and 520 nm emission (Synergy HT™, Bio-Tek Instruments, Winooski, Vt.).

Total sulfated glycosaminoglycan (GAG) content was measured at days 3, 14, and 28 using the 1,9 dimethylmethylene blue (DMMB) assay (Farndale et al. 1982). The DMMB dye was reduced to pH 1.5 and absorbance was determined at 595 nm to minimize the formation of CMC carboxyl groups-DMMB dye complexes (Enobakhare et al. 1996). GAG values were determined using a chondroitin-6 sulfate standard curve (Sigma).

Collagen production was quantified at day 28 via indirect ELISAs using monoclonal antibodies to type I collagen (COL I, Sigma) and type II collagen (COL II) (II-II6B3, Developmental Studies Hybridoma Bank, University of Iowa, Iowa City, Iowa) based on previous protocols (Chou et al. 2008). Protein values for each sample were determined using a standard curve generated from bovine COL I and COL II (Rockland Immunochemicals, Gilbertsville, Pa.). Absorbance was determined at 450 nm DNA, GAG, and collagen content are presented normalized to wet weight.

Histology and Immunohistochemistry

Constructs were fixed for 45 minutes in acid formalin at room temperature and processed for paraffin embedding after graded serial ethanol dehydration. Samples were sectioned at a thickness of 8 μm, and hematoxylin and eosin staining was conducted to visualize cellular distribution throughout the hydrogel Immunohistochemical analyses were performed to assess extracellular matrix accumulation according to previous studies (Chou et al. 2008). Briefly, monoclonal antibodies to COL I, COL II, and chondroitin sulfate proteoglycan (CSPG, Sigma) were used. A peroxidase-based system (Vectastain Elite ABC, Vector Labs) and 3,3' diaminobenzidine as the chromagen were used to visualize ECM localization. Non-immune controls were processed without primary antibody. Samples were viewed with a Zeiss Axioskop 40 optical microscope and images were captured using AxioVision software.

Mechanical Testing

Unconfined compression testing was conducted on CMC hydrogels (n=5) at day 28 as previously described (Chou and Nicoll; Soltz and Ateshian 1998). Briefly, the unconfined compression testing protocol was comprised of a creep test followed by a multi-ramp stress-relaxation test. The creep test consisted of a 1 g tare load at 10 μm/s ramp velocity for 1800 seconds until equilibrium was reached (equilibrium criteria: <10 μm change in 10 minutes). The multi-ramp stress-relaxation test consisted of three 5% strain ramps, each followed by a 2000 second relaxation period (equilibrium criteria: <0.5 g change in 10 minutes). Equilibrium stress was calculated at each ramp using surface area measurements and plotted against the applied strain. An average equilibrium Young's modulus was calculated from the stress versus strain curves and reported for each sample.

Statistical Analysis

A three-way ANOVA was used to determine the effects of time, medium, and TGF-$\beta_3$ on wet weight, dry weight, $Q_w$, DNA content, and GAG accumulation (n=4). A two-way ANOVA was used to determine the effects of medium and TGF-$\beta_3$ on collagen content (n=4), hydrogel diameter, thickness, and $E_y$ (n=5) at day 28. Significance was set at p<0.05. Data represent the mean±standard deviation.

Figure 20:
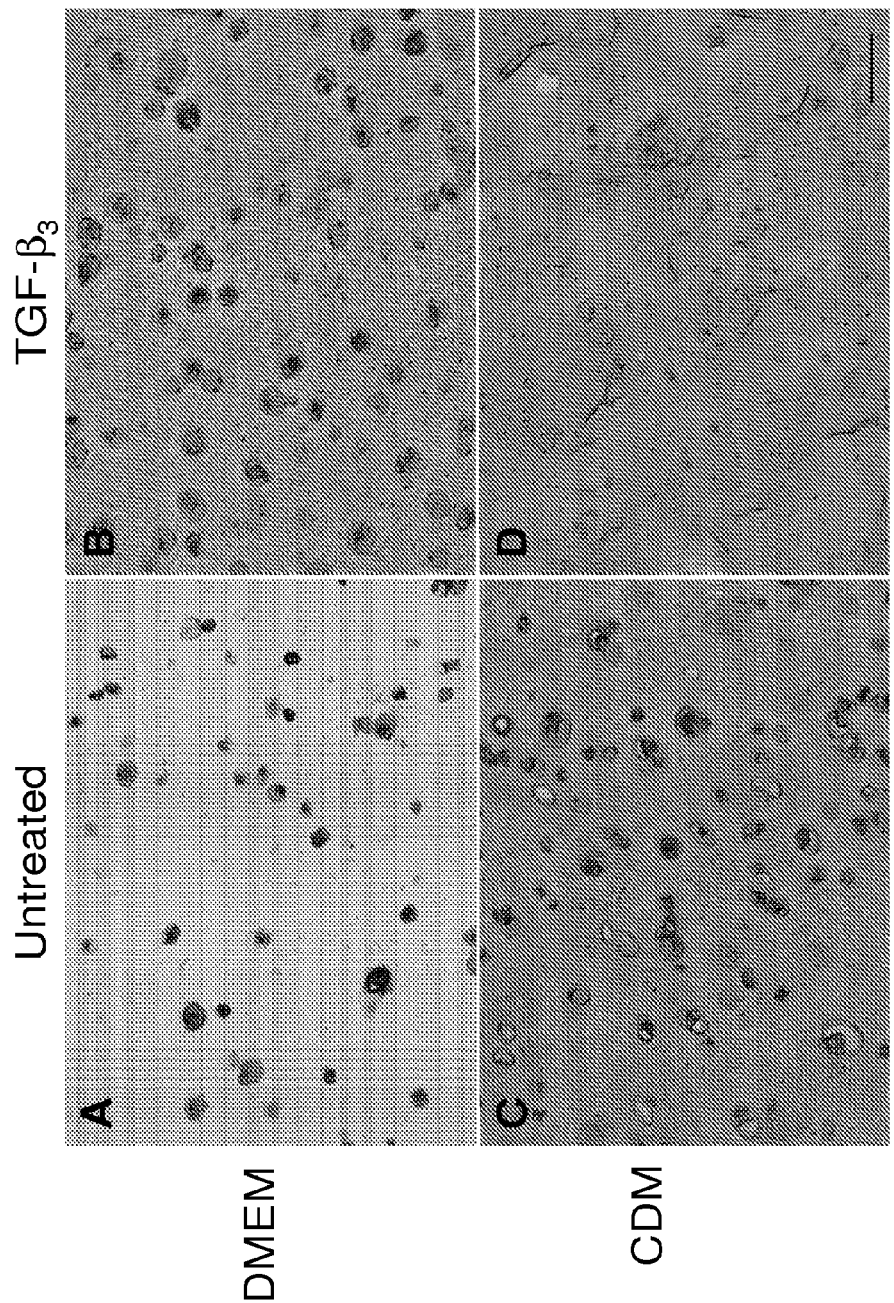
FIG. 20 shows immunohistochemical staining for chondroitin sulfate proteoglycan content of CMC constructs at day 28 cultured in DMEM (A, B) and CDM (C, D) with (B, D) and without (A, C) TGF-β3. Bar=50 m.
Figure 21:
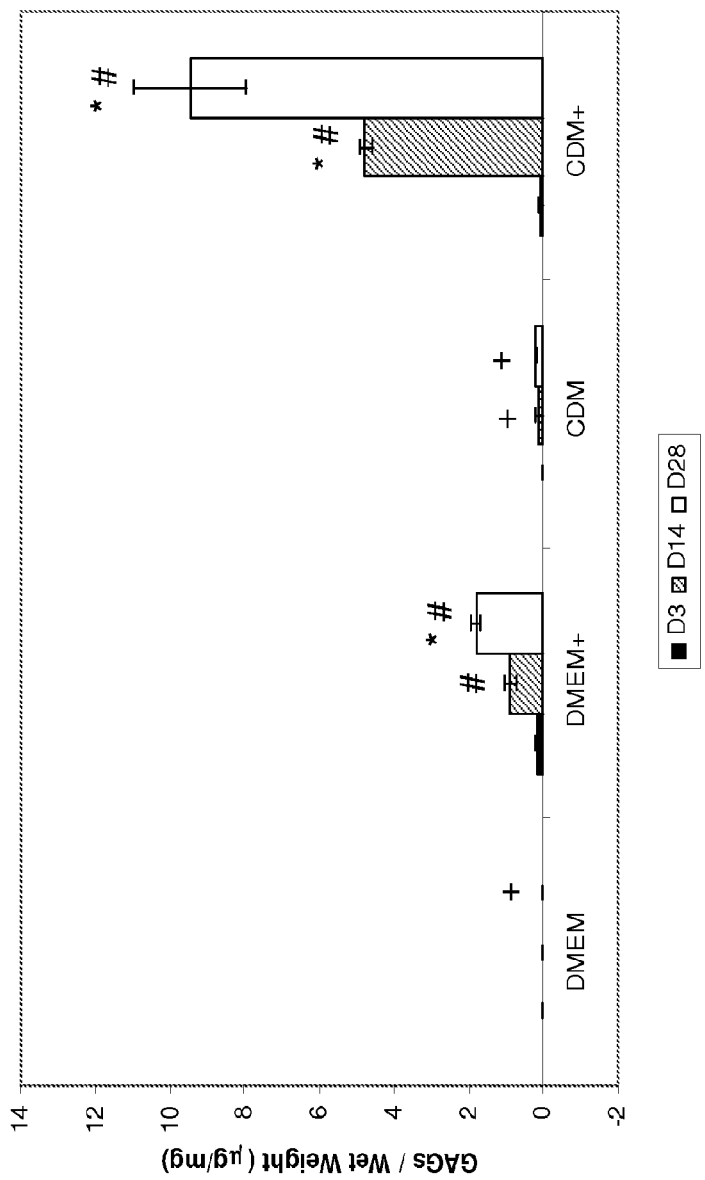
FIG. 21 shows normalized GAG content (n=4) at days 3, 14, and 28 as a function of medium formulation. * Significant vs. all other time points within group; + Significant vs. corresponding treated group within time point (i.e., DMEM vs. DMEM+); # Significant vs. opposing media type within time point (i.e., DMEM+ vs. CDM+).

Results 250 kDa CMC was methacrylated at a 5.63% modification, as verified by $^1$H-NMR (data not shown). Constructs were isolated at days 3, 14, and 28 to determine swelling ratio measurements, DNA content, and GAG accumulation. Treated groups (DMEM+ and CDM+) experienced significant increases in both wet weight and dry weight at each time point, while measurements for untreated groups (DMEM and CDM) remained unchanged from day 3 values and significantly lower in comparison (FIG. 23). A significant temporal decrease in $Q_w$ was measured for DMEM+ and CDM+ groups, whereas the swelling ratio of untreated samples stayed constant and markedly higher. DNA content significantly decreased in DMEM constructs but increased in both TGF-$\beta_3$ supplemented groups and was highest in DMEM+ samples. GAG accumulation significantly increased over time in both treated groups and was highest in CDM+ constructs (FIG. 21). There was no quantifiable GAG content in untreated DMEM hydrogels and no effect of medium formulation when comparing untreated groups (DMEM versus CDM). Immunohistochemical analyses conducted at day 28 revealed limited pericellular deposition of CSPG in untreated DMEM samples with enhanced interritorial staining for DMEM+ constructs (FIG. 20A, B). This staining was more intense in CDM samples but CSPG deposition remained highly concentrated in lacuna. However, CDM+ groups exhibited uniform interritorial CSPG accumulation throughout the construct (FIG. 20D).

Figure 19:
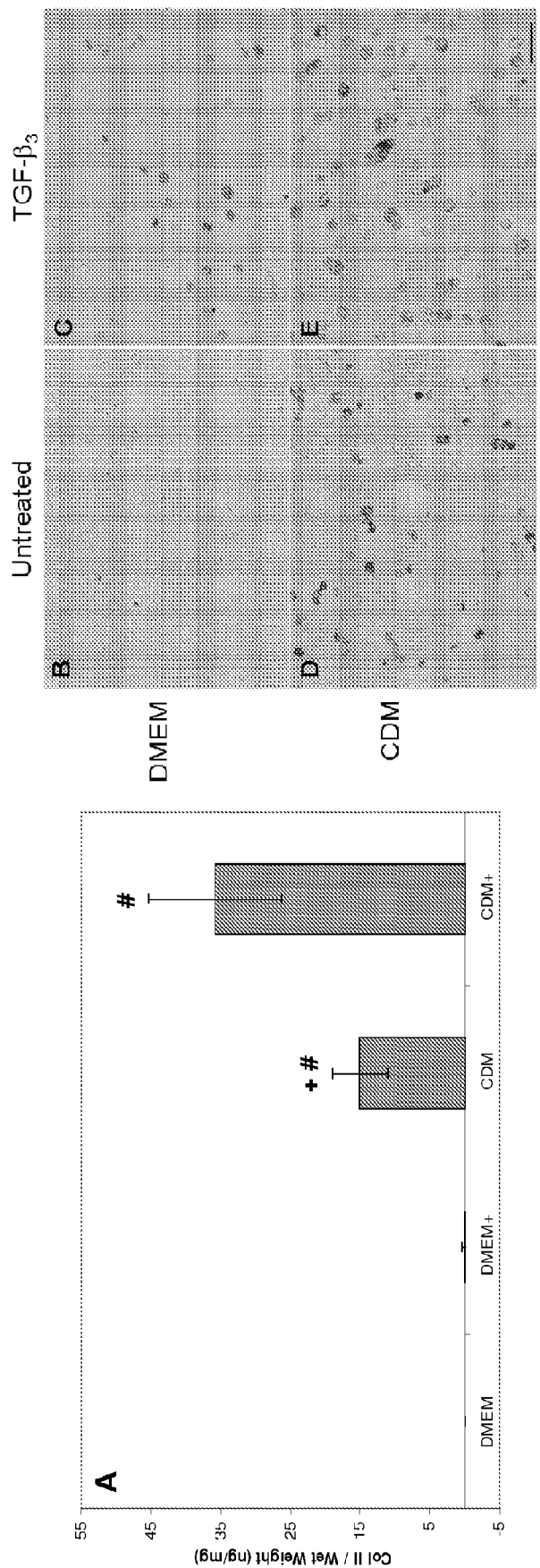
FIG. 19 shows normalized COL II content (n=4) (A) and immunohistochemical staining at day 28 for CMC constructs cultured in DMEM (B, C) and CDM (D, E) with (C, E) and without (B, D) TGF-β3. Bar=50 m. + Significant vs. corresponding treated group (i.e., DMEM vs. DMEM+); # Significant vs. opposing media type (i.e., DMEM+ vs. CDM+).

Day 28 ELISA quantification of type II collagen accumulation was significantly greater in both CDM groups in comparison to DMEM samples and was highest in CDM+ constructs (FIG. 19A). There was no detectable COL II in untreated DMEM samples. These measurements were verified by COL II immunohistochemistry. By day 28, there was still no detectable COL II staining in untreated DMEM samples and light, pericellular staining at the periphery of DMEM+ samples (FIG. 19B, C). Both CDM groups were positive for COL II throughout the construct, with the most intense staining observed for CDM+ samples (FIG. 19E).

Figure 18:
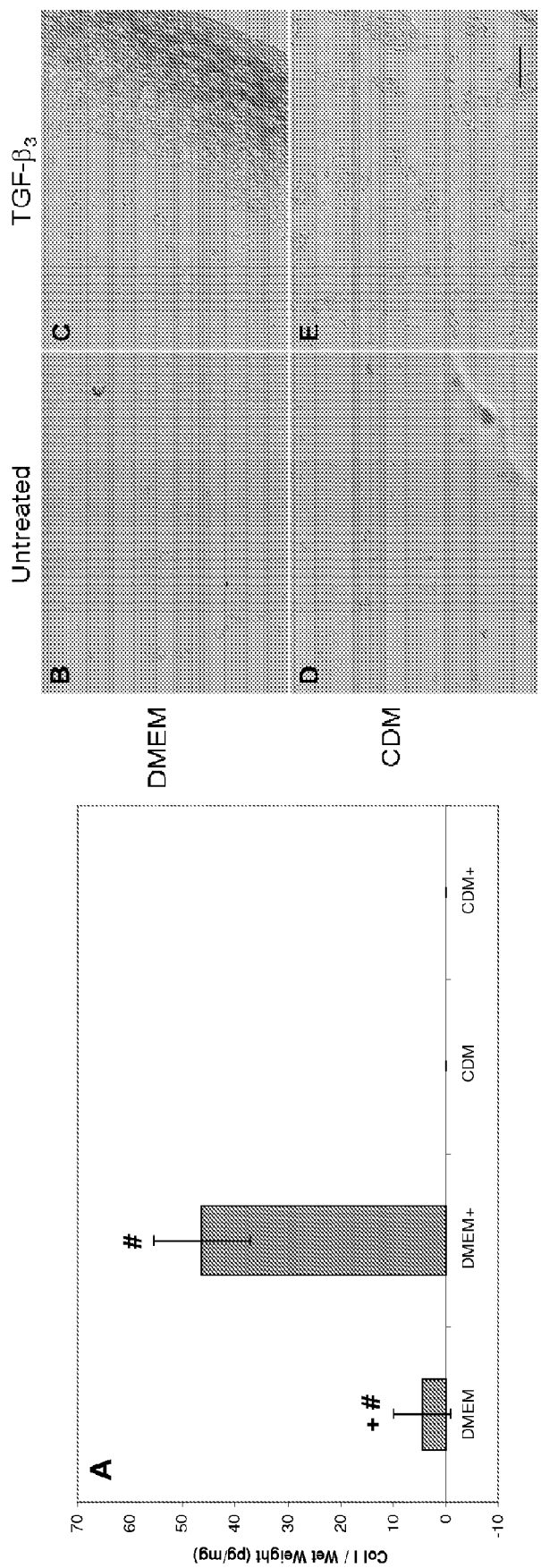
FIG. 18 shows normalized COL I content (n=4) (A) and immunohistochemical staining of the scaffold periphery at day 28 for CMC constructs cultured in DMEM (B, C) and CDM (D, E) with (C, E) and without (B, D) TGF-β3. Bar=50 m. + Significant vs. corresponding treated group (i.e., DMEM vs. DMEM+); # Significant vs. opposing media type (i.e., DMEM+ vs. CDM+).

Day 28 type I collagen quantification was highest in DMEM+ samples, while there was no detectable COL I in either CDM group (FIG. 18A) Immunohistochemical analysis revealed light COL I deposition at the periphery of DMEM and DMEM+ samples (FIG. 18B, C). In addition, DMEM+ constructs possessed a thick (100-200 μm) outer ring of fibroblastic cells, which stained positive for COL I (FIG. 18C), while there was minimal COL I staining observed in either CDM group.

Figure 17:
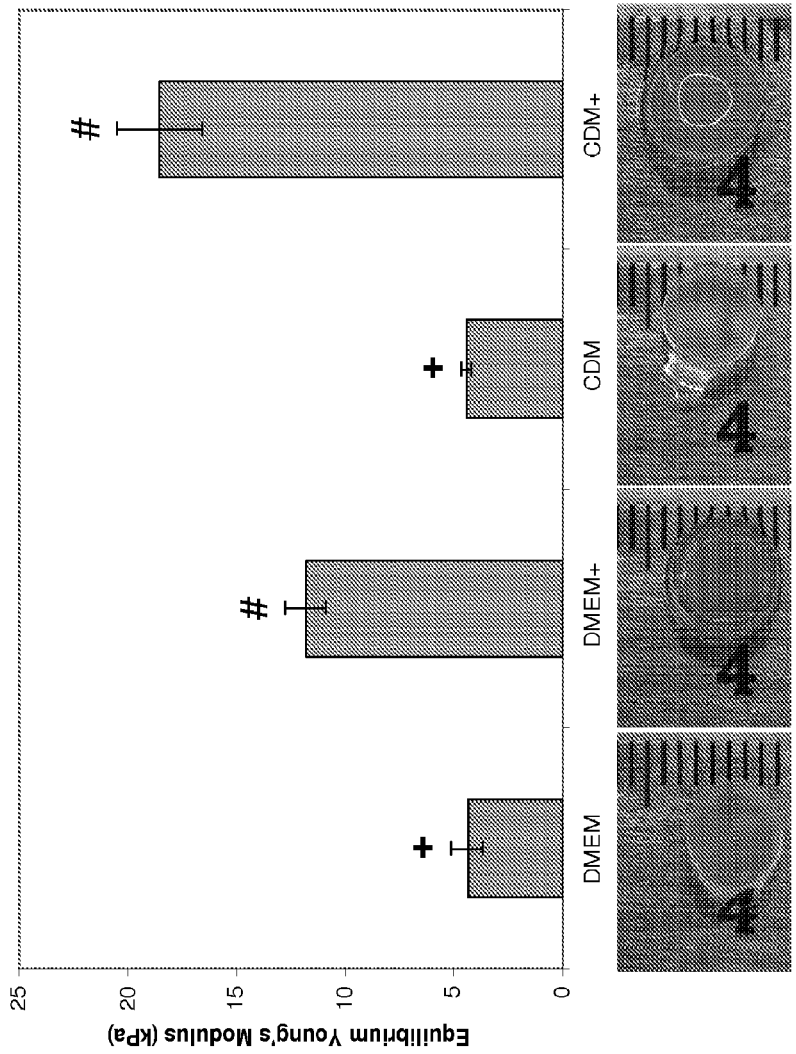
FIG. 17 shows Equilibrium Young's modulus of CMC constructs (n=5) at day 28 as a function of medium formulation with representative corresponding stereomicrograph images shown below. Scale is in mm + Significant vs. corresponding treated group (i.e., DMEM vs. DMEM+); # Significant vs. opposing media type (i.e., DMEM+ vs. CDM+).
Figure 24:
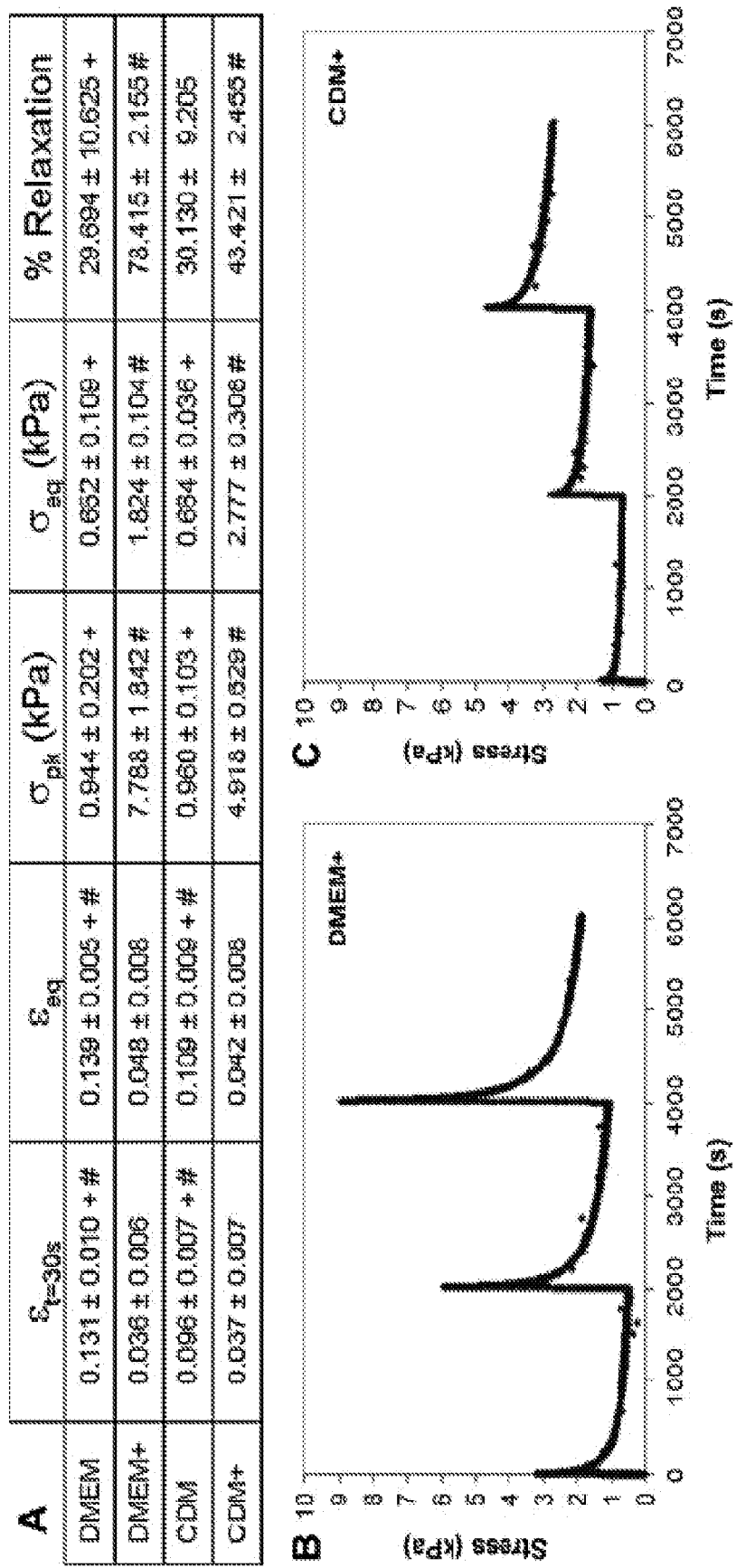
FIG. 24 shows mechanical properties (A) of CMC constructs (n=5) at day 28, as demonstrated by the transient (30 s after loading) and equilibrium creep strain ($\epsilon_{t=30s}$ and $\epsilon_{eq}$, respectively), and peak stress ($\sigma_{pk}$), equilibrium stress ($\sigma_{eq}$), and percent relaxation at 15% strain. Representative stress versus time curves for DMEM+(B) and CDM+(C) samples. +: Significant versus corresponding treated group (i.e., DMEM vs. DMEM+). #: Significant versus opposing media type (i.e., DMEM+vs. CDM+).

Constructs were tested in unconfined compression at day 28 to determine mechanical properties. Hydrogel diameter and thickness measurements in both treated groups (DMEM+ and CDM+) were significantly greater than those for untreated groups and were largest in CDM+constructs, as treated constructs grew in both the radial and axial directions (FIG. 22). Sample thickness was assessed 30 s after the application of a 1 g tare load in the creep test to determine the transient strain in the axial direction, $\epsilon_t$=30 s. Untreated DMEM constructs experienced the most deformation shortly after loading (13.074±0.958%) while there was no significant difference between treated groups (DMEM+vs. CDM+, 3.642±0.623%) (FIG. 24). The equilibrium creep strain followed the same trend, with untreated DMEM samples greater than untreated groups. However, DMEM+constructs were unable to sustain this stress and displayed a rapid relaxation which corresponded to the highest % relaxation among all groups. Conversely, CDM+samples maintained a higher $\sigma_{eq}$ to $\sigma_{pk}$ ratio, with a % relaxation significantly less than DMEM+scaffolds. The equilibrium Young's modulus was significantly greater in both treated groups and was highest for CDM+(CDM+: 18.54±1.92 kPa; DMEM+: 11.82±0.92 kPa) (FIG. 17). Treated constructs were most opaque in gross appearance, with the highest degree of opacity observed for CDM+constructs. There was no effect of medium formulation on diameter, thickness, $\sigma_{eq}$, $\sigma_{pk}$, % relaxation, or Ey values when comparing untreated groups (DMEM vs. CDM).

This study is the first to examine the effects of media formulation and growth factor supplementation on NP cells encapsulated in CMC hydrogels. This work has illustrated the benefit of TGF-$\beta_3$ supplementation to a chemically-defined, serum-free medium, resulting in increased GAG and COL II accumulation and enhanced functional properties (i.e., $E_y$), showing an alternate medium formulation for use in NP tissue engineering applications.

This study examined the effects of two variables, supplementation with TGF-$\beta_3$ and medium formulation, comparing a standard serum-containing medium to a chemically defined, serum-free medium. In general, the addition of TGF-$\beta_3$ resulted in enhanced matrix deposition by both groups (DMEM+ and CDM+). As a result of the marked temporal increases in wet and dry weight, $Q_w$ for both TGF-$\beta_3$-treated groups at day 28 was ~22, closely approaching the $Q_w$ for native NP tissue (~19).

Although similar overall trends were observed in comparison to untreated controls in both DMEM+ and CDM+ samples, the effect of base medium (DMEM versus CDM) was most remarkable when examining the measurements most often associated with the NP phenotype. The combination of CDM and TGF-$\beta_3$ resulted in dramatic increases in GAG accumulation. By day 28, CDM+ samples retained 9.46±1.51 µg GAG/mg wet weight, while DMEM+ constructs retained over five times less (1.80±0.11 µg/mg) (FIG. 21). This 28-day value for CDM+ samples is ~40% that obtained after 16 weeks of in vivo culture (24.14±0.71 µg/mg) using a subcutaneous murine pouch model for NP cells cast in alginate at a similar initial seeding density. In addition, when normalized to dry weight, CDM+ GAG content approaches 210 µg/mg, also ~40% of that measured in the native NP (~550 µg/mg).

The distinct effects of CDM media were also evident when examining collagen production. There was no quantifiable COL II present in either untreated or TGF-$\beta_3$-treated DMEM groups, while both CDM groups displayed significant accumulation which was highest in CDM+ samples, though limited to pericellular deposition. In addition, TGF-$\beta_3$ supplementation to DMEM resulted in a multilayered ring of fibroblastic cells encapsulating the CMC hydrogel which stained positive for COL I, contrary to the native NP phenotype (FIG. 18C).

TGF-$\beta_3$ supplementation resulted in increased mechanical properties in both DMEM+ and CDM+ groups. However, consistent with trends observed in GAG and COL II quantification, $E_y$ values were largest for CDM+ samples and significantly greater than all other groups. Although untreated CDM constructs produced small, but quantifiable amounts of COL II by day 28 which was significantly greater than that produced by untreated DMEM samples, there was no difference in $E_y$ between the untreated groups. This may be due to the fact that both DMEM and CDM constructs produced similar amounts of water-retaining GAGs, as evidenced by the DMMB assay allowing the scaffold to resist comparable compressive forces. Although immunohistochemical staining indicates a better distributed, more intense CSPG matrix in untreated CDM (FIG. 20A, C), this technique employs a specific antibody to CSPG, while the DMMB assay recognizes all sulfated GAGs.

The inventors of the instant application have found that although the combination of TGF-$\beta_1$ and bFGF produced the greatest increase in retained chondroitin sulfate, this value never exceeded 10% of the native NP, even after 60 days of culture. This work noted morphologic changes characteristic of nutrient deficiency when cultured in 1% FBS; however, cell morphology returned to normal when the low serum medium was supplemented with TGF-$\beta_1$.

The inventors of the instant application have shown a differential effect of both medium formulation and TGF-$\beta_3$ supplementation on cell-laden CMC hydrogel constructs, producing marked increases in GAG and COL II content and $E_y$.

Taken together, these findings suggest that photocrosslinked CMC hydrogels support functional ECM assembly by encapsulated NP cells when cultured in serum-free, chemically-defined medium supplemented with TGF-$\beta_3$.

Example 7

Figure 26:
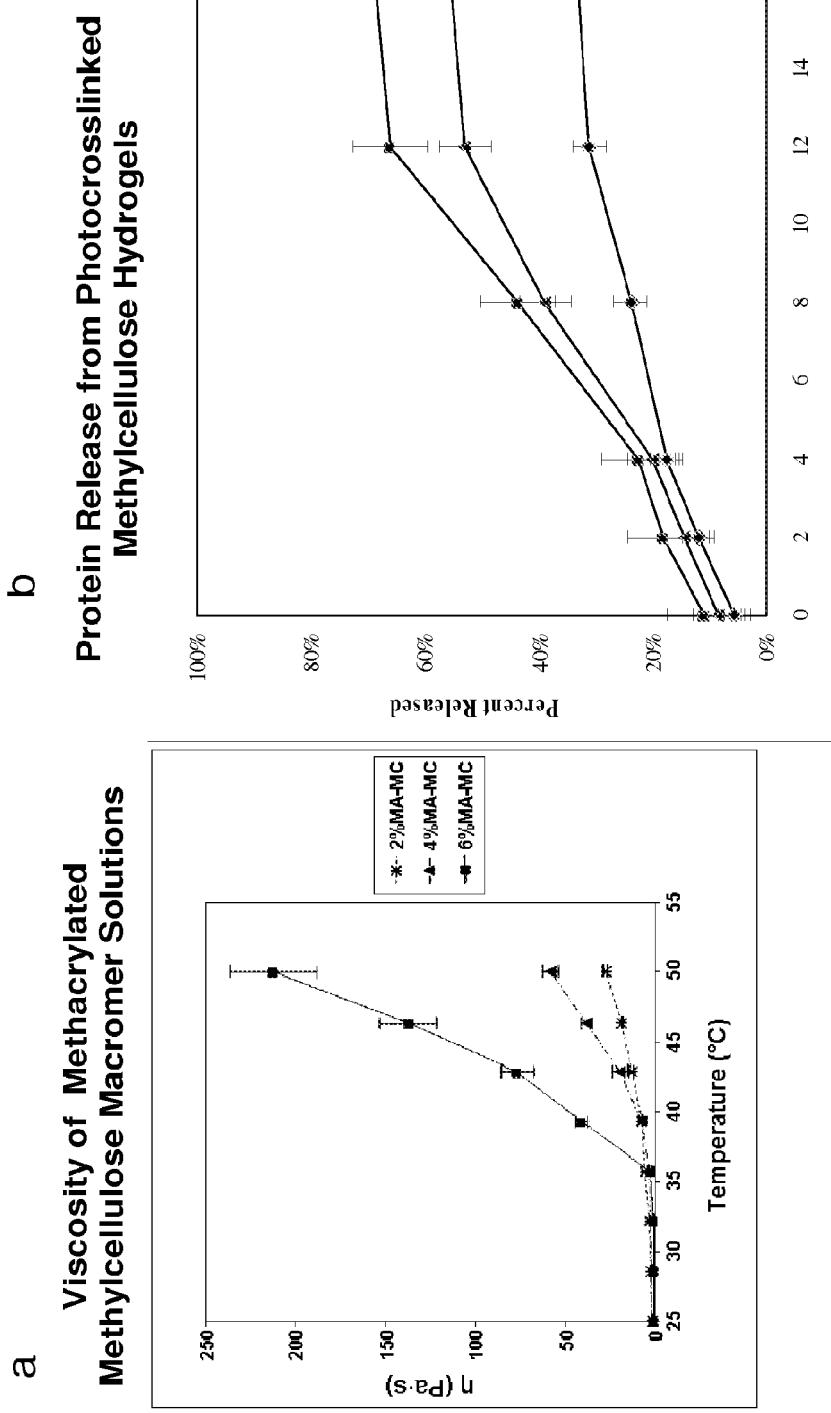
FIG. 26 shows photocrosslinked cellulosic hydrogels. (A) Viscosity of methacrylated methylcellulose macromer solutions. (B) Protein release from photocrosslinked methylcellulose hydrogels.

In Situ Redox Initiated Gelation of CMC Constructs and Protein Release from MC Hydrogels FIG. 25 shows CMC hydrogels crosslinked using redox initiators. FIG. 25 clearly demonstrates that a redox initiation system (APS/TEMED) can be used to form covalently crosslinked carboxymethylcellulose hydrogels (2% and 2.5% macromer concentration) for nucleus pulposus cell encapsulation and as an injectable system as a soft tissue filler. FIG. 26A shows that methacrylated methylcellulose at different macromer concentrations (2, 4, 6%) prior to polymerization exhibits a viscosity (up to 250 Pa·s) in the range of commercially available injectable fillers (50 to 900 Pa·s) at body temperature. FIG. 26B shows that photocrosslinked methylcellulose hydrogels at varying macromer concentrations can be used for controlled delivery of proteins using bovine serum albumin as a model protein.

Having described preferred embodiments of the invention with reference to the accompanying drawings, it is to be understood that the invention is not limited to the precise embodiments, and that various changes and modifications may be effected therein by those skilled in the art without departing from the scope or spirit of the invention as defined in the appended claims.

What is claimed is:

1. A biomaterial composition comprising (1) a cellulose derivative polymer wherein an unprotected group on the cellulose derivative polymer backbone is substituted with covalently bound crosslinkable groups, wherein said crosslinkable groups are methacrylate groups, and wherein the cellulose derivative is methyl cellulose, carboxymethyl cellulose, or a combination thereof; and (2) a redox initiator system including an oxidizing agent and a reducing agent, wherein the oxidizing agent and reducing agent are separated within the composition, wherein the degree of substitution is between about 1 and about 6%, wherein the polymer concentration is between about 2 and about 15% (w/v), and wherein the initial molecular weight of the polymer is between about 10 and about 1000 kDa.

2. The composition of claim 1, wherein the cellulose derivative is a combination of methyl cellulose and carboxymethyl cellulose.

3. The composition of claim 1, further comprising a peptide, a morphogen, a growth factor, a hormone, a small molecule, a toxin, a cytokine, or a combination thereof.

4. The composition of claim 1, further comprising a cell.

5. The composition of claim 4, wherein the cell is a nucleus pulposus (NP) cell or a human dermal fibroblast (hDFs) cell.

6. The composition of claim 4, wherein the cell is a stem cell, a dendritic cell, a mesenchymal stem cell, a nucleus pulposus cell, a progenitor cell, a dermis-derived fibroblastic cell, a cartilaginous tissue cell or their combination.

7. The composition of claim 6, wherein the cartilaginous tissue cell is an articular cartilage, a meniscus, a temporomandibular joint cartilage, an intervertebral disc, or their combination.

8. An implant comprising the biomaterial composition of claim 1.

9. A method for reparing, reconstructung, or augmenting a soft tissue, in a subject, the method comprising the steps of: identifying a volume of interest to be repaired, reconstructed or augmented in the subject; filling the volume with the biomaterial composition of claim 1; crosslinking the polymer by combining the oxidizing and reducing agents to form a crosslinked hydrogel.

10. The method of claim 9, further comprising modifying a physico-chemical property of the hydrogel to comply with a mechanical requirement of the soft tissue.

11. The method of claim 10, whereby the physico-chemical property is G', G", tan-d, Young's modulus, glass transition temperature, inherent viscosity, effective molecular weight, thermodynamic compatibility, free volume, swelling ratio, constitutive model parameter or their combination.

12. The method of claim 9, further comprising the steps of solubilizing the substituted polymer backbone and suspending in the solubilized polymer, a composition comprising a cell type, for which growth is sought.

13. The method of claim 12, whereby the cell is a stem cell, a dendritic cell, a mesenchymal stem cell, a nucleus pulposus cell, a progenitor cell, a dermis-derived fibroblastic cell, a cartilaginous tissue cell or their combination.

14. The method of claim 9, further comprising the steps of solubilizing the substituted polymer backbone and suspending in the solubilized polymer, a composition comprising a peptide, a morphogen, a growth factor, a hormone, a small molecule, a toxin, a cytokine, or a combination thereof.

15. The method of claim 9, whereby the soft tissue is a breast, a testicle, a labia, a skin layer, a lip, or their combination.

16. The method according to claim 9, whereby the hydrogel has an elastic modulus (G') of between about 2 to 400 Pa.

17. The method of claim 9, whereby the step of filling the volume of interest is carried out in-situ.

18. The method of claim 9, whereby the step of filling the volume of interest is preceded by a step of making a mold of the volume of interest.

19. The method of claim 9, whereby the step of forming a hydrogel is followed by a step of implanting the hydrogel in the identified volume of interest.

20. A method of making an implant for the reconstruction, repair or augmentation of a soft tissue in a subject, comprising the steps of: making a three-dimensional mold of a soft tissue region of the subject sought to be repaired, reconstructed or augmented; transferring the biomaterial composition of claim 1 into the three-dimensional mold of the soft tissue region of said subject; and crosslinking the polymer by combining the oxidizing and reducing agents to form a crosslinked hydrogel.

21. A method of making an implant for the reconstruction, repair or augmentation of a soft tissue in a subject, comprising the steps of: injecting the biomaterial composition of claim 1 into the soft tissue location sought to be repaired, reconstructed or augmented; and crosslinking the biomaterial composition by combining the oxidizing and reducing agents to form a crosslinked hydrogel.

22. A method of smoothing skin wrinkles in a subject, comprising the steps of: injecting into a skin wrinkle a biomaterial composition of claim 1; and crosslinking the biomaterial composition by combining the oxidizing and reducing agents to form a crosslinked hydrogel in-situ.

23. A method for restoring a structure and a mechanical function of a intervertebral disc comprising the step of encapsulating a nucleus pulposus (NP) cell with the biomaterial composition of claim 1.

24. The method of claim 23, wherein the encapsulation is performed in presence of a media comprising a transforming growth factor-beta 3 (TGF-beta 3).

25. The composition of claim 1, wherein the oxidizing agent is ammonium persulfate or sodium persulfate.

26. The composition of claim 1, wherein the reducing agent is ascorbic acid, sodium ascorbate, or magnesium ascorbate.

27. The composition of claim 1, wherein the reducing agent is N,N,N',N'-tetramethylethylenediamine (TEMED).

28. The composition of claim 27, wherein the oxidizing agent is ammonium persulfate.

29. The composition of claim 1, wherein the oxidizing agent is ammonium persulfate and the reducing agent is ascorbic acid.

* * * * *